US012268437B2

(12) United States Patent
Koop et al.

(10) Patent No.: US 12,268,437 B2
(45) Date of Patent: Apr. 8, 2025

(54) ELECTRIC FIELD APPLICATION FOR SINGLE SHOT CARDIAC ABLATION BY IRREVERSIBLE ELECTROPORATION

(71) Applicant: Boston Scientific Scimed Inc, Maple Grove, MN (US)

(72) Inventors: Brendan E. Koop, Ham Lake, MN (US); Andrew L. De Kock, Ham Lake, MN (US); Allan C. Shuros, St Paul, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 444 days.

(21) Appl. No.: 17/381,953

(22) Filed: Jul. 21, 2021

(65) Prior Publication Data

US 2022/0022952 A1    Jan. 27, 2022

Related U.S. Application Data

(60) Provisional application No. 63/056,017, filed on Jul. 24, 2020.

(51) Int. Cl.
*A61B 18/00* (2006.01)
*A61B 18/12* (2006.01)
*A61B 18/14* (2006.01)

(52) U.S. Cl.
CPC ...... *A61B 18/1492* (2013.01); *A61B 18/1206* (2013.01); *A61B 2018/00577* (2013.01);
(Continued)

(58) Field of Classification Search
CPC ...... A61B 2018/00613; A61B 18/1206; A61B 2018/124–128; A61N 1/327
See application file for complete search history.

(56) References Cited

U.S. PATENT DOCUMENTS 4,200,104 A    4/1980 Harris
4,470,407 A    9/1984 Hussein
(Continued)

FOREIGN PATENT DOCUMENTS

AU    741167 B2    11/2001
EP    1042990 A1    10/2000
(Continued)

OTHER PUBLICATIONS

Du Pre, B.C. et al., "Minimal coronary artery damage by myocardial electroporation ablation," Europace, 15(1):144-149 (2013).
(Continued)

*Primary Examiner* — Linda C Dvorak
*Assistant Examiner* — Davina E. Lee
(74) *Attorney, Agent, or Firm* — Nelson Mullins Riley & Scarborough LLP

(57) ABSTRACT

Disclosed herein are apparatus, systems, and methods for ablating tissue in a patient by electroporation. Embodiments generally include an ablation catheter having a hand, a shaft, and an electroporation electrode arrangement. The shaft has a distal end and defines a longitudinal axis of the ablation catheter. The electroporation electrode arrangement is at the distal end of the shaft and is configured to generate a multidirectional electric field when at least one pulse sequence is delivered thereto. The multidirectional electric field includes at least two of the following directions relative to the longitudinal axis: generally axial, circumferential, and transverse. The electroporation electrode arrangement is configured to operatively couple to an electroporation generator that is configured to generate the at least one pulse sequence and is configured to receive the at least one pulse sequence from the electroporation generator.

10 Claims, 11 Drawing Sheets

(52) U.S. Cl.
CPC .............. *A61B 2018/00613* (2013.01); *A61B 2018/1253* (2013.01); *A61B 2018/126* (2013.01); *A61B 2018/1266* (2013.01); *A61B 2018/1467* (2013.01)

(56) References Cited

U.S. PATENT DOCUMENTS

| | | |
|---|---|---|
| 4,739,759 A | 4/1988 | Rexroth et al. |
| 5,234,004 A | 8/1993 | Hascoet et al. |
| 5,242,441 A | 9/1993 | Avitall |
| 5,257,635 A | 11/1993 | Langberg |
| 5,281,213 A | 1/1994 | Milder et al. |
| 5,304,214 A | 4/1994 | Deford et al. |
| 5,306,296 A | 4/1994 | Wright et al. |
| 5,334,183 A | 8/1994 | Wuchinich |
| 5,334,193 A | 8/1994 | Nardella |
| 5,341,807 A | 8/1994 | Nardella |
| 5,342,301 A | 8/1994 | Saab |
| 5,398,683 A | 3/1995 | Edwards et al. |
| 5,443,463 A | 8/1995 | Stern et al. |
| 5,454,370 A | 10/1995 | Avitall |
| 5,515,848 A | 5/1996 | Corbett et al. |
| 5,531,685 A | 7/1996 | Hemmer et al. |
| 5,545,161 A | 8/1996 | Imran |
| 5,578,040 A | 11/1996 | Smith |
| 5,617,854 A | 4/1997 | Munsif |
| 5,624,430 A | 4/1997 | Eton et al. |
| 5,667,491 A | 9/1997 | Pliquett et al. |
| 5,672,170 A | 9/1997 | Cho et al. |
| 5,700,243 A | 12/1997 | Narciso, Jr. |
| 5,702,438 A | 12/1997 | Avitall |
| 5,706,823 A | 1/1998 | Wodlinger |
| 5,722,400 A | 3/1998 | Ockuly et al. |
| 5,722,402 A | 3/1998 | Swanson et al. |
| 5,749,914 A | 5/1998 | Janssen |
| 5,779,699 A | 7/1998 | Lipson |
| 5,788,692 A | 8/1998 | Campbell et al. |
| 5,810,762 A | 9/1998 | Hofmann |
| 5,833,710 A | 11/1998 | Jacobson |
| 5,836,874 A | 11/1998 | Swanson et al. |
| 5,836,942 A | 11/1998 | Netherly et al. |
| 5,836,947 A | 11/1998 | Fleischman et al. |
| 5,843,154 A | 12/1998 | Osypka |
| 5,849,028 A | 12/1998 | Chen |
| 5,860,974 A | 1/1999 | Abele |
| 5,863,291 A | 1/1999 | Schaer |
| 5,868,736 A | 2/1999 | Swanson et al. |
| 5,871,523 A | 2/1999 | Fleischman et al. |
| 5,876,336 A | 3/1999 | Swanson et al. |
| 5,885,278 A | 3/1999 | Fleischman |
| 5,895,404 A | 4/1999 | Ruiz |
| 5,899,917 A | 5/1999 | Edwards et al. |
| 5,904,709 A | 5/1999 | Arndt et al. |
| 5,916,158 A | 6/1999 | Webster, Jr. |
| 5,916,213 A | 6/1999 | Haissaguerre et al. |
| 5,921,924 A | 7/1999 | Avitall |
| 5,928,269 A | 7/1999 | Alt |
| 5,928,270 A | 7/1999 | Ramsey, III |
| 5,938,660 A | 8/1999 | Swartz et al. |
| 6,002,955 A | 12/1999 | Willems et al. |
| 6,006,131 A | 12/1999 | Cooper et al. |
| 6,009,351 A | 12/1999 | Flachman |
| 6,014,579 A | 1/2000 | Pomeranz et al. |
| 6,029,671 A | 2/2000 | Stevens et al. |
| 6,033,403 A | 3/2000 | Tu et al. |
| 6,035,238 A | 3/2000 | Ingle et al. |
| 6,045,550 A | 4/2000 | Simpson et al. |
| 6,068,653 A | 5/2000 | LaFontaine |
| 6,071,274 A | 6/2000 | Thompson et al. |
| 6,071,281 A | 6/2000 | Burnside et al. |
| 6,074,389 A | 6/2000 | Levine et al. |
| 6,076,012 A | 6/2000 | Swanson et al. |
| 6,090,104 A | 7/2000 | Webster, Jr. |
| 6,096,036 A | 8/2000 | Bowe et al. |
| 6,113,595 A | 9/2000 | Muntermann |
| 6,119,041 A | 9/2000 | Pomeranz et al. |
| 6,120,500 A | 9/2000 | Bednarek et al. |
| 6,142,993 A | 11/2000 | Whayne et al. |
| 6,146,381 A | 11/2000 | Bowe et al. |
| 6,164,283 A | 12/2000 | Lesh |
| 6,167,291 A | 12/2000 | Barajas et al. |
| 6,171,305 B1 | 1/2001 | Sherman |
| 6,216,034 B1 | 4/2001 | Hofmann et al. |
| 6,219,582 B1 | 4/2001 | Hofstad et al. |
| 6,223,085 B1 | 4/2001 | Dann et al. |
| 6,231,518 B1 | 5/2001 | Grabek et al. |
| 6,245,064 B1 | 6/2001 | Lesh et al. |
| 6,251,107 B1 | 6/2001 | Schaer |
| 6,251,109 B1 | 6/2001 | Hassett et al. |
| 6,251,128 B1 | 6/2001 | Knopp et al. |
| 6,270,476 B1 | 8/2001 | Santoianni et al. |
| 6,272,384 B1 | 8/2001 | Simon et al. |
| 6,287,306 B1 | 9/2001 | Kroll et al. |
| 6,314,963 B1 | 11/2001 | Vaska et al. |
| 6,322,559 B1 | 11/2001 | Daulton et al. |
| 6,350,263 B1 | 2/2002 | Wetzig et al. |
| 6,370,412 B1 | 4/2002 | Armoundas et al. |
| 6,391,024 B1 | 5/2002 | Sun et al. |
| 6,447,505 B2 | 9/2002 | Mcgovern et al. |
| 6,464,699 B1 | 10/2002 | Swanson |
| 6,470,211 B1 | 10/2002 | Ideker et al. |
| 6,502,576 B1 | 1/2003 | Lesh |
| 6,503,247 B2 | 1/2003 | Swartz et al. |
| 6,517,534 B1 | 2/2003 | Mcgovern et al. |
| 6,527,724 B1 | 3/2003 | Fenici |
| 6,527,767 B2 | 3/2003 | Wang et al. |
| 6,592,581 B2 | 7/2003 | Bowe |
| 6,595,991 B2 | 7/2003 | Toellner et al. |
| 6,607,520 B2 | 8/2003 | Keane |
| 6,613,046 B1 | 9/2003 | Jenkins et al. |
| 6,623,480 B1 | 9/2003 | Kuo et al. |
| 6,638,278 B2 | 10/2003 | Falwell et al. |
| 6,666,863 B2 | 12/2003 | Wentzel et al. |
| 6,669,693 B2 | 12/2003 | Friedman |
| 6,702,811 B2 | 3/2004 | Stewart et al. |
| 6,719,756 B1 | 4/2004 | Muntermann |
| 6,723,092 B2 | 4/2004 | Brown et al. |
| 6,728,563 B2 | 4/2004 | Rashidi |
| 6,743,225 B2 | 6/2004 | Sanchez et al. |
| 6,743,226 B2 | 6/2004 | Cosman et al. |
| 6,743,239 B1 | 6/2004 | Kuehn et al. |
| 6,764,486 B2 | 7/2004 | Natale |
| 6,780,181 B2 | 8/2004 | Kroll et al. |
| 6,805,128 B1 | 10/2004 | Pless et al. |
| 6,807,447 B2 | 10/2004 | Griffin, III |
| 6,892,091 B1 | 5/2005 | Ben-Haim et al. |
| 6,893,438 B2 | 5/2005 | Hall et al. |
| 6,926,714 B1 | 8/2005 | Sra |
| 6,955,173 B2 | 10/2005 | Lesh |
| 6,960,206 B2 | 11/2005 | Keane |
| 6,960,207 B2 | 11/2005 | Vanney et al. |
| 6,972,016 B2 | 12/2005 | Hill et al. |
| 6,973,339 B2 | 12/2005 | Govari |
| 6,979,331 B2 | 12/2005 | Hintringer et al. |
| 6,984,232 B2 | 1/2006 | Vanney et al. |
| 6,985,776 B2 | 1/2006 | Kane et al. |
| 7,001,383 B2 | 2/2006 | Keidar |
| 7,041,095 B2 | 5/2006 | Wang et al. |
| 7,113,831 B2 | 9/2006 | Hooven |
| 7,171,263 B2 | 1/2007 | Darvish et al. |
| 7,182,725 B2 | 2/2007 | Bonan et al. |
| 7,195,628 B2 | 3/2007 | Falkenberg |
| 7,207,988 B2 | 4/2007 | Leckrone et al. |
| 7,207,989 B2 | 4/2007 | Pike et al. |
| 7,229,402 B2 | 6/2007 | Diaz et al. |
| 7,229,437 B2 | 6/2007 | Johnson et al. |
| 7,250,049 B2 | 7/2007 | Roop et al. |
| 7,285,116 B2 | 10/2007 | De et al. |
| 7,285,119 B2 | 10/2007 | Stewart et al. |
| 7,326,208 B2 | 2/2008 | Vanney et al. |
| 7,346,379 B2 | 3/2008 | Eng et al. |
| 7,367,974 B2 | 5/2008 | Haemmerich et al. |
| 7,374,567 B2 | 5/2008 | Heuser |
| 7,387,629 B2 | 6/2008 | Vanney et al. |

(56) References Cited

U.S. PATENT DOCUMENTS

| | | |
|---|---|---|
| 7,387,630 B2 | 6/2008 | Mest |
| 7,387,636 B2 | 6/2008 | Cohn et al. |
| 7,416,552 B2 | 8/2008 | Paul et al. |
| 7,419,477 B2 | 9/2008 | Simpson et al. |
| 7,419,489 B2 | 9/2008 | Vanney et al. |
| 7,422,591 B2 | 9/2008 | Phan |
| 7,429,261 B2 | 9/2008 | Kunis et al. |
| 7,435,248 B2 | 10/2008 | Taimisto et al. |
| 7,513,896 B2 | 4/2009 | Orszulak |
| 7,527,625 B2 | 5/2009 | Knight et al. |
| 7,578,816 B2 | 8/2009 | Boveja et al. |
| 7,588,567 B2 | 9/2009 | Boveja et al. |
| 7,623,899 B2 | 11/2009 | Worley et al. |
| 7,678,108 B2 | 3/2010 | Chrisitian et al. |
| 7,681,579 B2 | 3/2010 | Schwartz |
| 7,771,421 B2 | 8/2010 | Stewart et al. |
| 7,805,182 B2 | 9/2010 | Weese et al. |
| 7,842,031 B2 | 11/2010 | Abboud et al. |
| 7,850,642 B2 | 12/2010 | Moll et al. |
| 7,850,685 B2 | 12/2010 | Kunis et al. |
| 7,857,808 B2 | 12/2010 | Oral et al. |
| 7,857,809 B2 | 12/2010 | Drysen |
| 7,869,865 B2 | 1/2011 | Govari et al. |
| 7,896,873 B2 | 3/2011 | Hiller et al. |
| 7,917,211 B2 | 3/2011 | Zacouto |
| 7,918,819 B2 | 4/2011 | Karmarkar et al. |
| 7,918,850 B2 | 4/2011 | Govari et al. |
| 7,922,714 B2 | 4/2011 | Stevens-Wright |
| 7,955,827 B2 | 6/2011 | Rubinsky et al. |
| 8,048,067 B2 | 11/2011 | Davalos et al. |
| 8,048,072 B2 | 11/2011 | Verin et al. |
| 8,100,895 B2 | 1/2012 | Panos et al. |
| 8,100,900 B2 | 1/2012 | Prinz et al. |
| 8,108,069 B2 | 1/2012 | Stahler et al. |
| 8,133,220 B2 | 3/2012 | Lee et al. |
| 8,137,342 B2 | 3/2012 | Crossman |
| 8,145,289 B2 | 3/2012 | Calabro' et al. |
| 8,147,486 B2 | 4/2012 | Honour et al. |
| 8,160,690 B2 | 4/2012 | Wilfley et al. |
| 8,175,680 B2 | 5/2012 | Panescu |
| 8,182,477 B2 | 5/2012 | Orszulak et al. |
| 8,206,384 B2 | 6/2012 | Falwell et al. |
| 8,206,385 B2 | 6/2012 | Stangenes et al. |
| 8,216,221 B2 | 7/2012 | Ibrahim et al. |
| 8,221,411 B2 | 7/2012 | Francischelli et al. |
| 8,226,648 B2 | 7/2012 | Paul et al. |
| 8,228,065 B2 | 7/2012 | Wirtz et al. |
| 8,235,986 B2 | 8/2012 | Kulesa et al. |
| 8,235,988 B2 | 8/2012 | Davis et al. |
| 8,251,986 B2 | 8/2012 | Chornenky et al. |
| 8,282,631 B2 | 10/2012 | Davalos et al. |
| 8,287,532 B2 | 10/2012 | Carroll et al. |
| 8,414,508 B2 | 4/2013 | Thapliyal et al. |
| 8,430,875 B2 | 4/2013 | Ibrahim et al. |
| 8,433,394 B2 | 4/2013 | Harlev et al. |
| 8,449,535 B2 | 5/2013 | Deno et al. |
| 8,454,594 B2 | 6/2013 | Demarais et al. |
| 8,463,368 B2 | 6/2013 | Harlev et al. |
| 8,475,450 B2 | 7/2013 | Govari et al. |
| 8,486,063 B2 | 7/2013 | Werneth et al. |
| 8,500,733 B2 | 8/2013 | Watson |
| 8,535,304 B2 | 9/2013 | Sklar et al. |
| 8,538,501 B2 | 9/2013 | Venkatachalam et al. |
| 8,562,588 B2 | 10/2013 | Hobbs et al. |
| 8,568,406 B2 | 10/2013 | Harlev et al. |
| 8,568,410 B2 | 10/2013 | Vakharia et al. |
| 8,571,635 B2 | 10/2013 | Mcgee |
| 8,571,647 B2 | 10/2013 | Harlev et al. |
| 8,579,897 B2 | 11/2013 | Vakharia et al. |
| 8,585,695 B2 | 11/2013 | Shih |
| 8,588,885 B2 | 11/2013 | Hall et al. |
| 8,597,288 B2 | 12/2013 | Christian |
| 8,608,735 B2 | 12/2013 | Govari et al. |
| 8,628,522 B2 | 1/2014 | Ibrahim et al. |
| 8,632,534 B2 | 1/2014 | Pearson et al. |
| 8,647,338 B2 | 2/2014 | Chornenky et al. |
| 8,708,952 B2 | 4/2014 | Cohen et al. |
| 8,734,442 B2 | 5/2014 | Cao et al. |
| 8,771,267 B2 | 7/2014 | Kunis et al. |
| 8,795,310 B2 | 8/2014 | Fung et al. |
| 8,808,273 B2 | 8/2014 | Caples et al. |
| 8,808,281 B2 | 8/2014 | Emmons et al. |
| 8,834,461 B2 | 9/2014 | Werneth et al. |
| 8,834,464 B2 | 9/2014 | Stewart et al. |
| 8,868,169 B2 | 10/2014 | Narayan et al. |
| 8,876,817 B2 | 11/2014 | Avitall et al. |
| 8,880,195 B2 | 11/2014 | Azure |
| 8,886,309 B2 | 11/2014 | Luther et al. |
| 8,903,488 B2 | 12/2014 | Callas et al. |
| 8,920,411 B2 | 12/2014 | Gelbart et al. |
| 8,926,589 B2 | 1/2015 | Govari |
| 8,932,287 B2 | 1/2015 | Gelbart et al. |
| 8,945,117 B2 | 2/2015 | Bencini |
| 8,979,841 B2 | 3/2015 | Kunis et al. |
| 8,986,278 B2 | 3/2015 | Fung et al. |
| 8,996,091 B2 | 3/2015 | De et al. |
| 9,002,442 B2 | 4/2015 | Harley et al. |
| 9,005,189 B2 | 4/2015 | Davalos et al. |
| 9,005,194 B2 | 4/2015 | Oral et al. |
| 9,011,425 B2 | 4/2015 | Fischer et al. |
| 9,044,245 B2 | 6/2015 | Condie et al. |
| 9,055,959 B2 | 6/2015 | Vaska et al. |
| 9,072,518 B2 | 7/2015 | Swanson |
| 9,078,667 B2 | 7/2015 | Besser et al. |
| 9,101,374 B1 | 8/2015 | Hoch et al. |
| 9,113,911 B2 | 8/2015 | Sherman |
| 9,119,533 B2 | 9/2015 | Ghaffari |
| 9,119,634 B2 | 9/2015 | Gelbart et al. |
| 9,131,897 B2 | 9/2015 | Harada et al. |
| 9,155,590 B2 | 10/2015 | Mathur |
| 9,162,037 B2 | 10/2015 | Belson et al. |
| 9,179,972 B2 | 11/2015 | Olson |
| 9,186,481 B2 | 11/2015 | Avitall et al. |
| 9,192,769 B2 | 11/2015 | Donofrio et al. |
| 9,204,916 B2 | 12/2015 | Lalonde |
| 9,211,405 B2 | 12/2015 | Mahapatra et al. |
| 9,216,055 B2 | 12/2015 | Spence et al. |
| 9,233,248 B2 | 1/2016 | Luther et al. |
| 9,237,926 B2 | 1/2016 | Nollert et al. |
| 9,262,252 B2 | 2/2016 | Kirkpatrick et al. |
| 9,277,957 B2 | 3/2016 | Long et al. |
| 9,282,910 B2 | 3/2016 | Narayan et al. |
| 9,289,258 B2 | 3/2016 | Cohen |
| 9,289,606 B2 | 3/2016 | Paul et al. |
| 9,295,516 B2 | 3/2016 | Pearson et al. |
| 9,301,801 B2 | 4/2016 | Scheib |
| 9,351,789 B2 | 5/2016 | Novichenok et al. |
| 9,375,268 B2 | 6/2016 | Long |
| 9,387,031 B2 | 7/2016 | Stewart et al. |
| 9,414,881 B2 | 8/2016 | Callas et al. |
| 9,468,495 B2 | 10/2016 | Kunis et al. |
| 9,474,486 B2 | 10/2016 | Eliason et al. |
| 9,474,574 B2 | 10/2016 | Ibrahim et al. |
| 9,480,525 B2 | 11/2016 | Lopes et al. |
| 9,486,272 B2 | 11/2016 | Bonyak et al. |
| 9,486,273 B2 | 11/2016 | Lopes et al. |
| 9,492,227 B2 | 11/2016 | Lopes et al. |
| 9,492,228 B2 | 11/2016 | Lopes et al. |
| 9,510,888 B2 | 12/2016 | Jean-Pierre |
| 9,517,103 B2 | 12/2016 | Panescu et al. |
| 9,526,573 B2 | 12/2016 | Lopes et al. |
| 9,532,831 B2 | 1/2017 | Reinders et al. |
| 9,539,010 B2 | 1/2017 | Gagner et al. |
| 9,554,848 B2 | 1/2017 | Stewart et al. |
| 9,554,851 B2 | 1/2017 | Sklar et al. |
| 9,700,368 B2 | 7/2017 | Callas et al. |
| 9,724,170 B2 | 8/2017 | Mickelsen |
| 9,757,193 B2 | 9/2017 | Zarins et al. |
| 9,782,099 B2 | 10/2017 | Williams et al. |
| 9,795,442 B2 | 10/2017 | Salahieh et al. |
| 9,801,681 B2 | 10/2017 | Laske et al. |
| 9,808,304 B2 | 11/2017 | Lalonde |
| 9,861,802 B2 | 1/2018 | Mickelsen |
| 9,913,685 B2 | 3/2018 | Clark et al. |

(56) References Cited

U.S. PATENT DOCUMENTS

| | | | |
|---|---|---|---|
| 9,931,487 B2 | 4/2018 | Quinn et al. | |
| 9,987,081 B1 | 6/2018 | Bowers et al. | |
| 9,999,465 B2 | 6/2018 | Long et al. | |
| 10,010,368 B2 | 7/2018 | Laske et al. | |
| 10,016,232 B1 | 7/2018 | Bowers et al. | |
| 10,130,423 B1 * | 11/2018 | Viswanathan | A61B 18/1492 |
| 10,172,673 B2 | 1/2019 | Viswanathan et al. | |
| 10,194,818 B2 | 2/2019 | Williams et al. | |
| 10,285,755 B2 | 5/2019 | Stewart et al. | |
| 10,322,286 B2 | 6/2019 | Viswanathan et al. | |
| 10,433,906 B2 | 10/2019 | Mickelsen | |
| 10,433,908 B2 | 10/2019 | Viswanathan et al. | |
| 10,512,505 B2 | 12/2019 | Raju | |
| 10,512,779 B2 | 12/2019 | Viswanathan et al. | |
| 10,517,672 B2 | 12/2019 | Long | |
| 10,617,467 B2 | 4/2020 | Viswanathan et al. | |
| 10,660,702 B2 | 5/2020 | Viswanathan et al. | |
| 2001/0000791 A1 | 5/2001 | Suorsa et al. | |
| 2001/0007070 A1 | 7/2001 | Stewart et al. | |
| 2001/0044624 A1 | 11/2001 | Seraj et al. | |
| 2002/0022839 A1 | 2/2002 | Stewart et al. | |
| 2002/0052602 A1 | 5/2002 | Wang et al. | |
| 2002/0058933 A1 | 5/2002 | Christopherson et al. | |
| 2002/0077627 A1 | 6/2002 | Johnson et al. | |
| 2002/0087169 A1 | 7/2002 | Brock et al. | |
| 2002/0091384 A1 | 7/2002 | Hooven et al. | |
| 2002/0095176 A1 | 7/2002 | Prestel | |
| 2002/0111618 A1 | 8/2002 | Stewart et al. | |
| 2002/0156526 A1 | 10/2002 | Hlavka et al. | |
| 2002/0161323 A1 | 10/2002 | Miller et al. | |
| 2002/0169445 A1 | 11/2002 | Jain et al. | |
| 2002/0177765 A1 | 11/2002 | Bowe et al. | |
| 2002/0183638 A1 | 12/2002 | Swanson | |
| 2003/0014098 A1 | 1/2003 | Quijano et al. | |
| 2003/0018374 A1 | 1/2003 | Paulos | |
| 2003/0023287 A1 | 1/2003 | Edwards et al. | |
| 2003/0028189 A1 | 2/2003 | Woloszko et al. | |
| 2003/0050637 A1 | 3/2003 | Maguire et al. | |
| 2003/0060856 A1 | 3/2003 | Chornenky et al. | |
| 2003/0114849 A1 | 6/2003 | Ryan | |
| 2003/0125729 A1 | 7/2003 | Hooven et al. | |
| 2003/0130598 A1 | 7/2003 | Manning et al. | |
| 2003/0130711 A1 | 7/2003 | Pearson et al. | |
| 2003/0204161 A1 | 10/2003 | Ferek-Petric | |
| 2003/0229379 A1 | 12/2003 | Maynard | |
| 2004/0039382 A1 | 2/2004 | Kroll et al. | |
| 2004/0049181 A1 | 3/2004 | Stewart et al. | |
| 2004/0049182 A1 | 3/2004 | Koblish et al. | |
| 2004/0082859 A1 | 4/2004 | Schaer | |
| 2004/0082948 A1 | 4/2004 | Stewart et al. | |
| 2004/0087939 A1 | 5/2004 | Eggers et al. | |
| 2004/0111087 A1 | 6/2004 | Stern et al. | |
| 2004/0199157 A1 | 10/2004 | Palanker et al. | |
| 2004/0231683 A1 | 11/2004 | Eng et al. | |
| 2004/0236360 A1 | 11/2004 | Cohn et al. | |
| 2004/0254607 A1 | 12/2004 | Wittenberger et al. | |
| 2004/0267337 A1 | 12/2004 | Hayzelden | |
| 2005/0033282 A1 | 2/2005 | Hooven | |
| 2005/0187545 A1 | 8/2005 | Hooven et al. | |
| 2005/0222632 A1 | 10/2005 | Obino | |
| 2005/0251130 A1 | 11/2005 | Boveja et al. | |
| 2005/0261672 A1 | 11/2005 | Deem et al. | |
| 2006/0009755 A1 | 1/2006 | Sra | |
| 2006/0009759 A1 | 1/2006 | Christian et al. | |
| 2006/0015095 A1 | 1/2006 | Desinger et al. | |
| 2006/0015165 A1 | 1/2006 | Bertolero et al. | |
| 2006/0024359 A1 | 2/2006 | Walker et al. | |
| 2006/0058781 A1 | 3/2006 | Long | |
| 2006/0111702 A1 | 5/2006 | Oral et al. | |
| 2006/0142801 A1 | 6/2006 | Demarais et al. | |
| 2006/0167448 A1 | 7/2006 | Kozel | |
| 2006/0217703 A1 | 9/2006 | Chornenky et al. | |
| 2006/0241734 A1 | 10/2006 | Marshall et al. | |
| 2006/0264752 A1 | 11/2006 | Rubinsky et al. | |
| 2006/0270900 A1 | 11/2006 | Chin et al. | |
| 2006/0287648 A1 | 12/2006 | Schwartz | |
| 2006/0293730 A1 | 12/2006 | Rubinsky et al. | |
| 2006/0293731 A1 | 12/2006 | Rubinsky et al. | |
| 2007/0005053 A1 | 1/2007 | Dando | |
| 2007/0021744 A1 | 1/2007 | Creighton | |
| 2007/0060989 A1 | 3/2007 | Deem et al. | |
| 2007/0066972 A1 | 3/2007 | Ormsby et al. | |
| 2007/0129721 A1 | 6/2007 | Phan et al. | |
| 2007/0129760 A1 | 6/2007 | Demarais et al. | |
| 2007/0156135 A1 | 7/2007 | Rubinsky et al. | |
| 2007/0167740 A1 | 7/2007 | Grunewald et al. | |
| 2007/0167940 A1 | 7/2007 | Stevens-Wright | |
| 2007/0173878 A1 | 7/2007 | Heuser | |
| 2007/0208329 A1 | 9/2007 | Ward et al. | |
| 2007/0225589 A1 | 9/2007 | Viswanathan | |
| 2007/0249923 A1 | 10/2007 | Keenan | |
| 2007/0260223 A1 | 11/2007 | Scheibe et al. | |
| 2007/0270792 A1 | 11/2007 | Hennemann et al. | |
| 2008/0009855 A1 | 1/2008 | Hamou | |
| 2008/0033426 A1 | 2/2008 | Machell | |
| 2008/0065061 A1 | 3/2008 | Viswanathan | |
| 2008/0086120 A1 | 4/2008 | Mirza et al. | |
| 2008/0091195 A1 | 4/2008 | Sliwa et al. | |
| 2008/0103545 A1 | 5/2008 | Bolea et al. | |
| 2008/0132885 A1 | 6/2008 | Rubinsky et al. | |
| 2008/0161789 A1 | 7/2008 | Thao et al. | |
| 2008/0172048 A1 | 7/2008 | Martin et al. | |
| 2008/0200913 A1 | 8/2008 | Viswanathan | |
| 2008/0208118 A1 | 8/2008 | Goldman | |
| 2008/0243214 A1 | 10/2008 | Koblish | |
| 2008/0281322 A1 | 11/2008 | Sherman et al. | |
| 2008/0300574 A1 | 12/2008 | Belson et al. | |
| 2008/0300588 A1 | 12/2008 | Groth et al. | |
| 2009/0024084 A1 | 1/2009 | Khosla et al. | |
| 2009/0048591 A1 | 2/2009 | Ibrahim et al. | |
| 2009/0062788 A1 | 3/2009 | Long et al. | |
| 2009/0076496 A1 | 3/2009 | Azure | |
| 2009/0076500 A1 | 3/2009 | Azure | |
| 2009/0105654 A1 | 4/2009 | Kurth et al. | |
| 2009/0138009 A1 | 5/2009 | Viswanathan et al. | |
| 2009/0149917 A1 | 6/2009 | Whitehurst et al. | |
| 2009/0163905 A1 | 6/2009 | Winkler et al. | |
| 2009/0228003 A1 | 9/2009 | Sinelnikov | |
| 2009/0240248 A1 | 9/2009 | Deford et al. | |
| 2009/0275827 A1 | 11/2009 | Aiken et al. | |
| 2009/0281477 A1 | 11/2009 | Mikus et al. | |
| 2009/0306651 A1 | 12/2009 | Schneider | |
| 2010/0004623 A1 | 1/2010 | Hamilton et al. | |
| 2010/0023004 A1 | 1/2010 | Francischelli et al. | |
| 2010/0137861 A1 | 6/2010 | Soroff et al. | |
| 2010/0185140 A1 | 7/2010 | Kassab et al. | |
| 2010/0185186 A1 | 7/2010 | Longoria | |
| 2010/0191112 A1 | 7/2010 | Demarais et al. | |
| 2010/0191232 A1 | 7/2010 | Boveda | |
| 2010/0241185 A1 | 9/2010 | Mahapatra et al. | |
| 2010/0261994 A1 | 10/2010 | Davalos et al. | |
| 2010/0274238 A1 | 10/2010 | Klimovitch | |
| 2010/0280513 A1 | 11/2010 | Juergen et al. | |
| 2010/0280539 A1 | 11/2010 | Miyoshi et al. | |
| 2010/0292687 A1 | 11/2010 | Kauphusman et al. | |
| 2010/0312096 A1 | 12/2010 | Guttman et al. | |
| 2010/0312300 A1 | 12/2010 | Ryu et al. | |
| 2011/0028962 A1 | 2/2011 | Werneth et al. | |
| 2011/0028964 A1 | 2/2011 | Edwards | |
| 2011/0040199 A1 | 2/2011 | Hopenfeld | |
| 2011/0098694 A1 | 4/2011 | Long | |
| 2011/0106221 A1 | 5/2011 | Neal et al. | |
| 2011/0130708 A1 | 6/2011 | Perry et al. | |
| 2011/0144524 A1 | 6/2011 | Fish et al. | |
| 2011/0144633 A1 | 6/2011 | Govari | |
| 2011/0160785 A1 | 6/2011 | Mori et al. | |
| 2011/0190659 A1 | 8/2011 | Long et al. | |
| 2011/0190727 A1 | 8/2011 | Edmunds et al. | |
| 2011/0213231 A1 | 9/2011 | Hall et al. | |
| 2011/0276047 A1 | 11/2011 | Sklar et al. | |
| 2011/0276075 A1 | 11/2011 | Fung et al. | |
| 2011/0288544 A1 | 11/2011 | Verin et al. | |
| 2011/0288547 A1 | 11/2011 | Morgan et al. | |
| 2011/0313417 A1 | 12/2011 | De et al. | |

(56) References Cited

U.S. PATENT DOCUMENTS

| | | |
|---|---|---|
| 2012/0029512 A1 | 2/2012 | Willard et al. |
| 2012/0046570 A1 | 2/2012 | Mllegas et al. |
| 2012/0053581 A1 | 3/2012 | Wittkampf et al. |
| 2012/0059255 A1 | 3/2012 | Paul et al. |
| 2012/0071872 A1 | 3/2012 | Rubinsky et al. |
| 2012/0078320 A1 | 3/2012 | Schotzko et al. |
| 2012/0078343 A1 | 3/2012 | Fish |
| 2012/0089089 A1 | 4/2012 | Swain et al. |
| 2012/0095459 A1 | 4/2012 | Callas et al. |
| 2012/0101413 A1 | 4/2012 | Beetel et al. |
| 2012/0158021 A1 | 6/2012 | Morrill |
| 2012/0165667 A1 | 6/2012 | Altmann et al. |
| 2012/0172859 A1 | 7/2012 | Condie et al. |
| 2012/0172867 A1 | 7/2012 | Ryu et al. |
| 2012/0197100 A1 | 8/2012 | Razavi et al. |
| 2012/0209260 A1 | 8/2012 | Lambert et al. |
| 2012/0220998 A1 | 8/2012 | Long et al. |
| 2012/0265198 A1 | 10/2012 | Crow et al. |
| 2012/0283582 A1 | 11/2012 | Mahapatra et al. |
| 2012/0303019 A1 | 11/2012 | Zhao et al. |
| 2012/0310052 A1 | 12/2012 | Mahapatra et al. |
| 2012/0310230 A1 | 12/2012 | Willis |
| 2012/0310237 A1 | 12/2012 | Swanson |
| 2012/0316557 A1 | 12/2012 | Sartor et al. |
| 2013/0030430 A1 | 1/2013 | Stewart et al. |
| 2013/0060247 A1 | 3/2013 | Sklar et al. |
| 2013/0060248 A1 | 3/2013 | Sklar et al. |
| 2013/0079768 A1 | 3/2013 | De et al. |
| 2013/0090651 A1 | 4/2013 | Smith |
| 2013/0096655 A1 | 4/2013 | Moffitt et al. |
| 2013/0103027 A1 | 4/2013 | Sklar et al. |
| 2013/0103064 A1 | 4/2013 | Arenson et al. |
| 2013/0131662 A1 | 5/2013 | Wittkampf |
| 2013/0158538 A1 | 6/2013 | Govari |
| 2013/0158621 A1 | 6/2013 | Ding et al. |
| 2013/0172715 A1 | 7/2013 | Just et al. |
| 2013/0172864 A1 | 7/2013 | Ibrahim et al. |
| 2013/0172875 A1 | 7/2013 | Govari et al. |
| 2013/0184702 A1 | 7/2013 | Neal et al. |
| 2013/0218157 A1 | 8/2013 | Callas et al. |
| 2013/0226174 A1 | 8/2013 | Brahim et al. |
| 2013/0237984 A1 | 9/2013 | Sklar |
| 2013/0253415 A1 | 9/2013 | Sano et al. |
| 2013/0296679 A1 | 11/2013 | Condie et al. |
| 2013/0310829 A1 | 11/2013 | Cohen |
| 2013/0317385 A1 | 11/2013 | Sklar et al. |
| 2013/0331831 A1 | 12/2013 | Werneth et al. |
| 2013/0338467 A1 | 12/2013 | Grasse et al. |
| 2014/0005664 A1 | 1/2014 | Govari et al. |
| 2014/0024911 A1 | 1/2014 | Harlev et al. |
| 2014/0039288 A1 | 2/2014 | Hue-Teh |
| 2014/0051993 A1 | 2/2014 | Mcgee |
| 2014/0052118 A1 | 2/2014 | Laske et al. |
| 2014/0052126 A1 | 2/2014 | Long et al. |
| 2014/0052216 A1 | 2/2014 | Long et al. |
| 2014/0058377 A1 | 2/2014 | Deem et al. |
| 2014/0081113 A1 | 3/2014 | Cohen et al. |
| 2014/0100563 A1 | 4/2014 | Govari et al. |
| 2014/0107644 A1 | 4/2014 | Falwell et al. |
| 2014/0142408 A1 | 5/2014 | De et al. |
| 2014/0148804 A1 | 5/2014 | Ward et al. |
| 2014/0163480 A1 | 6/2014 | Govari et al. |
| 2014/0163546 A1 | 6/2014 | Govari et al. |
| 2014/0171942 A1 | 6/2014 | Werneth et al. |
| 2014/0180035 A1 | 6/2014 | Anderson |
| 2014/0187916 A1 | 7/2014 | Clark et al. |
| 2014/0194716 A1 | 7/2014 | Diep et al. |
| 2014/0194867 A1 | 7/2014 | Fish et al. |
| 2014/0200567 A1 | 7/2014 | Cox et al. |
| 2014/0235986 A1 | 8/2014 | Harlev et al. |
| 2014/0235988 A1 | 8/2014 | Ghosh |
| 2014/0235989 A1 | 8/2014 | Wodlinger et al. |
| 2014/0243851 A1 | 8/2014 | Cohen et al. |
| 2014/0253140 A1 | 9/2014 | Gilbert |
| 2014/0276760 A1 | 9/2014 | Bonyak et al. |
| 2014/0276782 A1 | 9/2014 | Paskar |
| 2014/0276791 A1 | 9/2014 | Ku et al. |
| 2014/0288556 A1 | 9/2014 | Ibrahim et al. |
| 2014/0303721 A1 | 10/2014 | Fung et al. |
| 2014/0343549 A1 | 11/2014 | Spear et al. |
| 2014/0364845 A1 | 12/2014 | Rashidi |
| 2014/0371613 A1 | 12/2014 | Narayan et al. |
| 2015/0005767 A1 | 1/2015 | Werneth et al. |
| 2015/0011995 A1 | 1/2015 | Avitall et al. |
| 2015/0066108 A1 | 3/2015 | Shi et al. |
| 2015/0119674 A1 | 4/2015 | Fischell et al. |
| 2015/0126840 A1 | 5/2015 | Thakur et al. |
| 2015/0133914 A1 | 5/2015 | Koblish |
| 2015/0138977 A1 | 5/2015 | Dacosta |
| 2015/0141978 A1 | 5/2015 | Subramaniam et al. |
| 2015/0141982 A1 | 5/2015 | Lee |
| 2015/0142041 A1 | 5/2015 | Kendale et al. |
| 2015/0148796 A1 | 5/2015 | Bencini |
| 2015/0150472 A1 | 6/2015 | Harlev et al. |
| 2015/0157402 A1 | 6/2015 | Kunis et al. |
| 2015/0157412 A1 | 6/2015 | Wallace et al. |
| 2015/0164584 A1 | 6/2015 | Davalos et al. |
| 2015/0173824 A1 | 6/2015 | Davalos et al. |
| 2015/0173828 A1 | 6/2015 | Avitall |
| 2015/0174404 A1 | 6/2015 | Rousso et al. |
| 2015/0182740 A1 | 7/2015 | Mickelsen |
| 2015/0196217 A1 | 7/2015 | Harlev et al. |
| 2015/0223726 A1 | 8/2015 | Harlev et al. |
| 2015/0230699 A1 | 8/2015 | Berul et al. |
| 2015/0258344 A1 | 9/2015 | Tandri et al. |
| 2015/0265342 A1 | 9/2015 | Long et al. |
| 2015/0265344 A1 | 9/2015 | Aktas et al. |
| 2015/0272656 A1 | 10/2015 | Chen |
| 2015/0272664 A9 | 10/2015 | Cohen |
| 2015/0272667 A1 | 10/2015 | Govari et al. |
| 2015/0282729 A1 | 10/2015 | Harlev et al. |
| 2015/0289923 A1 | 10/2015 | Davalos et al. |
| 2015/0304879 A1 | 10/2015 | Dacosta |
| 2015/0320481 A1 | 11/2015 | Cosman et al. |
| 2015/0321021 A1 | 11/2015 | Tandri et al. |
| 2015/0342532 A1 | 12/2015 | Basu et al. |
| 2015/0343212 A1 | 12/2015 | Rousso et al. |
| 2015/0351836 A1 | 12/2015 | Prutchi |
| 2015/0359583 A1 | 12/2015 | Swanson |
| 2016/0000500 A1 | 1/2016 | Salahieh et al. |
| 2016/0008061 A1 | 1/2016 | Fung et al. |
| 2016/0008065 A1 | 1/2016 | Gliner et al. |
| 2016/0029960 A1 | 2/2016 | Toth et al. |
| 2016/0038772 A1 | 2/2016 | Thapliyal et al. |
| 2016/0051204 A1 | 2/2016 | Harlev et al. |
| 2016/0051324 A1 | 2/2016 | Stewart et al. |
| 2016/0058493 A1 | 3/2016 | Neal et al. |
| 2016/0058506 A1 | 3/2016 | Spence et al. |
| 2016/0066993 A1 | 3/2016 | Avitall et al. |
| 2016/0074679 A1 | 3/2016 | Thapliyal et al. |
| 2016/0095531 A1 | 4/2016 | Narayan et al. |
| 2016/0095642 A1 | 4/2016 | Deno et al. |
| 2016/0095653 A1 | 4/2016 | Lambert et al. |
| 2016/0100797 A1 | 4/2016 | Mahapatra et al. |
| 2016/0100884 A1 | 4/2016 | Fay et al. |
| 2016/0106498 A1 | 4/2016 | Highsmith et al. |
| 2016/0106500 A1 | 4/2016 | Olson |
| 2016/0113709 A1* | 4/2016 | Maor ................ A61B 18/1492 606/41 |
| 2016/0113712 A1 | 4/2016 | Cheung et al. |
| 2016/0120564 A1 | 5/2016 | Kirkpatrick et al. |
| 2016/0128770 A1 | 5/2016 | Afonso et al. |
| 2016/0166167 A1 | 6/2016 | Narayan et al. |
| 2016/0166310 A1 | 6/2016 | Stewart et al. |
| 2016/0166311 A1 | 6/2016 | Long et al. |
| 2016/0174865 A1 | 6/2016 | Stewart et al. |
| 2016/0183877 A1 | 6/2016 | Williams et al. |
| 2016/0184003 A1 | 6/2016 | Srimathveeravalli et al. |
| 2016/0184004 A1 | 6/2016 | Hull et al. |
| 2016/0213282 A1 | 7/2016 | Leo et al. |
| 2016/0220307 A1 | 8/2016 | Miller et al. |
| 2016/0235470 A1 | 8/2016 | Callas et al. |
| 2016/0249972 A1 | 9/2016 | Klink |
| 2016/0256682 A1 | 9/2016 | Paul et al. |

(56) References Cited

U.S. PATENT DOCUMENTS

| | | |
|---|---|---|
| 2016/0287314 A1 | 10/2016 | Arena et al. |
| 2016/0310211 A1 | 10/2016 | Long |
| 2016/0324564 A1 | 11/2016 | Gerlach et al. |
| 2016/0324573 A1 | 11/2016 | Mickelson et al. |
| 2016/0331441 A1 | 11/2016 | Konings |
| 2016/0331459 A1 | 11/2016 | Townley et al. |
| 2016/0338770 A1 | 11/2016 | Bar-Tal et al. |
| 2016/0354142 A1 | 12/2016 | Pearson et al. |
| 2016/0361109 A1 | 12/2016 | Weaver et al. |
| 2017/0001016 A1 | 1/2017 | De Ridder |
| 2017/0035499 A1* | 2/2017 | Stewart ............. A61B 18/1206 |
| 2017/0042449 A1 | 2/2017 | Deno et al. |
| 2017/0042615 A1 | 2/2017 | Salahieh et al. |
| 2017/0056648 A1 | 3/2017 | Syed et al. |
| 2017/0065330 A1 | 3/2017 | Mickelson et al. |
| 2017/0065339 A1* | 3/2017 | Mickelson ......... A61B 18/1492 |
| 2017/0065340 A1 | 3/2017 | Long |
| 2017/0065343 A1 | 3/2017 | Mickelson |
| 2017/0071543 A1 | 3/2017 | Basu et al. |
| 2017/0095291 A1 | 4/2017 | Harrington et al. |
| 2017/0105793 A1 | 4/2017 | Cao et al. |
| 2017/0120048 A1 | 5/2017 | He et al. |
| 2017/0146584 A1 | 5/2017 | Daw et al. |
| 2017/0151014 A1 | 6/2017 | Perfler |
| 2017/0151029 A1 | 6/2017 | Mickelson |
| 2017/0172654 A1 | 6/2017 | Wittkampf et al. |
| 2017/0181795 A1 | 6/2017 | Debruyne |
| 2017/0189097 A1 | 7/2017 | Mswanathan et al. |
| 2017/0215953 A1 | 8/2017 | Long et al. |
| 2017/0245928 A1 | 8/2017 | Xiao et al. |
| 2017/0246455 A1 | 8/2017 | Athos et al. |
| 2017/0312024 A1 | 11/2017 | Harlev et al. |
| 2017/0312025 A1 | 11/2017 | Harlev et al. |
| 2017/0312027 A1 | 11/2017 | Harlev et al. |
| 2018/0001056 A1 | 1/2018 | Leeflang et al. |
| 2018/0028252 A1 | 2/2018 | Lalonde |
| 2018/0042674 A1 | 2/2018 | Mickelson |
| 2018/0042675 A1 | 2/2018 | Long |
| 2018/0043153 A1* | 2/2018 | Viswanathan ..... A61B 18/1492 |
| 2018/0064488 A1 | 3/2018 | Long et al. |
| 2018/0085160 A1 | 3/2018 | Viswanathan et al. |
| 2018/0093088 A1 | 4/2018 | Mickelson |
| 2018/0133460 A1 | 5/2018 | Townley et al. |
| 2018/0161093 A1 | 6/2018 | Basu et al. |
| 2018/0168511 A1 | 6/2018 | Hall et al. |
| 2018/0184982 A1 | 7/2018 | Basu et al. |
| 2018/0193090 A1 | 7/2018 | De et al. |
| 2018/0200497 A1 | 7/2018 | Mickelson |
| 2018/0235496 A1 | 8/2018 | Wu et al. |
| 2018/0256109 A1 | 9/2018 | Wu et al. |
| 2018/0280080 A1 | 10/2018 | Govari et al. |
| 2018/0303488 A1 | 10/2018 | Hill |
| 2018/0303543 A1 | 10/2018 | Stewart et al. |
| 2018/0311497 A1 | 11/2018 | Viswanathan et al. |
| 2018/0344202 A1 | 12/2018 | Bar-Tal et al. |
| 2018/0344393 A1 | 12/2018 | Gruba et al. |
| 2018/0360531 A1 | 12/2018 | Holmes et al. |
| 2018/0360534 A1 | 12/2018 | Teplitsky et al. |
| 2019/0015007 A1 | 1/2019 | Rottmann et al. |
| 2019/0015638 A1 | 1/2019 | Gruba et al. |
| 2019/0030328 A1 | 1/2019 | Stewart et al. |
| 2019/0046791 A1 | 2/2019 | Ebbers et al. |
| 2019/0069949 A1 | 3/2019 | Vrba et al. |
| 2019/0069950 A1 | 3/2019 | Viswanathan et al. |
| 2019/0076179 A1 | 3/2019 | Babkin et al. |
| 2019/0125439 A1 | 5/2019 | Rohl et al. |
| 2019/0125788 A1 | 5/2019 | Gruba et al. |
| 2019/0143106 A1 | 5/2019 | Dewitt et al. |
| 2019/0151015 A1 | 5/2019 | Viswanathan et al. |
| 2019/0175263 A1 | 6/2019 | Altmann et al. |
| 2019/0183378 A1 | 6/2019 | Mosesov et al. |
| 2019/0183567 A1 | 6/2019 | Govari et al. |
| 2019/0192223 A1 | 6/2019 | Rankin |
| 2019/0201089 A1 | 7/2019 | Waldstreicher et al. |
| 2019/0201688 A1 | 7/2019 | Olson |
| 2019/0209235 A1 | 7/2019 | Stewart et al. |
| 2019/0223948 A1 | 7/2019 | Stewart et al. |
| 2019/0231421 A1 | 8/2019 | Viswanathan et al. |
| 2019/0231425 A1 | 8/2019 | Waldstreicher et al. |
| 2019/0254735 A1 | 8/2019 | Stewart et al. |
| 2019/0269912 A1 | 9/2019 | Viswanathan et al. |
| 2019/0298442 A1 | 10/2019 | Ogata et al. |
| 2019/0307500 A1 | 10/2019 | Byrd et al. |
| 2019/0343580 A1 | 11/2019 | Nguyen et al. |
| 2019/0350647 A1 | 11/2019 | Ramberg et al. |
| 2019/0350649 A1 | 11/2019 | Sutermeister et al. |
| 2020/0008869 A1 | 1/2020 | Byrd |
| 2020/0008870 A1 | 1/2020 | Gruba et al. |
| 2020/0009378 A1 | 1/2020 | Stewart et al. |
| 2020/0038104 A1 | 2/2020 | Mickelson |
| 2020/0046423 A1 | 2/2020 | Viswanathan et al. |
| 2020/0093539 A1 | 3/2020 | Long et al. |
| 2022/0071699 A1 | 3/2022 | Viswanathan |
| 2022/0133405 A1 | 5/2022 | Mickelson |

FOREIGN PATENT DOCUMENTS

| | | |
|---|---|---|
| EP | 1125549 A2 | 8/2001 |
| EP | 0797956 B1 | 6/2003 |
| EP | 1340469 A1 | 9/2003 |
| EP | 1127552 B1 | 6/2006 |
| EP | 1803411 A2 | 7/2007 |
| EP | 1009303 B1 | 6/2009 |
| EP | 2213729 A2 | 8/2010 |
| EP | 2382935 A1 | 11/2011 |
| EP | 2425871 A2 | 3/2012 |
| EP | 2532320 A2 | 12/2012 |
| EP | 2587275 A1 | 5/2013 |
| EP | 2663227 A1 | 11/2013 |
| EP | 1909678 B1 | 1/2014 |
| EP | 2217165 B1 | 3/2014 |
| EP | 2376193 B1 | 3/2014 |
| EP | 2708181 A1 | 3/2014 |
| EP | 2777579 A1 | 9/2014 |
| EP | 2777585 A1 | 9/2014 |
| EP | 2934307 A1 | 10/2015 |
| EP | 3056242 A1 | 8/2016 |
| EP | 3111871 A1 | 1/2017 |
| EP | 3151773 B1 | 4/2018 |
| EP | 3656329 A1 | 5/2020 |
| JP | 2000-508196 A | 7/2000 |
| JP | 2005-516666 A | 6/2005 |
| JP | 2006-506184 A | 2/2006 |
| JP | 2008-538997 A | 11/2008 |
| JP | 2009-500129 A | 1/2009 |
| JP | 2011-509158 A | 3/2011 |
| JP | 2012-050538 A | 3/2012 |
| WO | 92/07622 A1 | 5/1992 |
| WO | 92/21278 A1 | 12/1992 |
| WO | 92/21285 A1 | 12/1992 |
| WO | 94/07413 A1 | 4/1994 |
| WO | 97/24073 A1 | 7/1997 |
| WO | 97/25917 A1 | 7/1997 |
| WO | 97/37719 A1 | 10/1997 |
| WO | 99/04851 A1 | 2/1999 |
| WO | 99/22659 A1 | 5/1999 |
| WO | 99/56650 A1 | 11/1999 |
| WO | 99/59486 A2 | 11/1999 |
| WO | 02/56782 A2 | 7/2002 |
| WO | 03/53289 A1 | 7/2003 |
| WO | 03/65916 A1 | 8/2003 |
| WO | 2004/045442 A1 | 6/2004 |
| WO | 2004/086994 A1 | 10/2004 |
| WO | 2005/046487 A1 | 5/2005 |
| WO | 2006/115902 A2 | 11/2006 |
| WO | 2007/006055 A2 | 1/2007 |
| WO | 2007/079438 A2 | 7/2007 |
| WO | 2009/082710 A1 | 7/2009 |
| WO | 2009/089343 A1 | 7/2009 |
| WO | 2009/137800 A2 | 11/2009 |
| WO | 2010/014480 A1 | 2/2010 |
| WO | 2011/028310 A1 | 3/2011 |
| WO | 2011/154805 A1 | 12/2011 |
| WO | 2012/051433 A2 | 4/2012 |

(56) References Cited

FOREIGN PATENT DOCUMENTS

| | | |
|---|---|---|
| WO | 2012/097067 A1 | 7/2012 |
| WO | 2012/153928 A2 | 11/2012 |
| WO | 2013/019385 A1 | 2/2013 |
| WO | 2014/025394 A1 | 2/2014 |
| WO | 2014/031800 A1 | 2/2014 |
| WO | 2014/036439 A2 | 3/2014 |
| WO | 2014/100579 A1 | 6/2014 |
| WO | 2014/160832 A2 | 10/2014 |
| WO | 2015/021113 A1 | 2/2015 |
| WO | 2015/066322 A1 | 5/2015 |
| WO | 2015/099786 A1 | 7/2015 |
| WO | 2015/103530 A1 | 7/2015 |
| WO | 2015/103574 A1 | 7/2015 |
| WO | 2015/130824 A1 | 9/2015 |
| WO | 2015/140741 A1 | 9/2015 |
| WO | 2015/143327 A1 | 9/2015 |
| WO | 2015/171921 A2 | 11/2015 |
| WO | 2015/175944 A1 | 11/2015 |
| WO | 2015/192018 A1 | 12/2015 |
| WO | 2015/192027 A1 | 12/2015 |
| WO | 2016/059027 A1 | 4/2016 |
| WO | 2016/060983 A1 | 4/2016 |
| WO | 2016/081650 A1 | 5/2016 |
| WO | 2016/090175 A1 | 6/2016 |
| WO | 2017/093926 A1 | 6/2017 |
| WO | 2017/119934 A1 | 7/2017 |
| WO | 2017/120169 A1 | 7/2017 |
| WO | 2017/192477 A1 | 11/2017 |
| WO | 2017/192495 A1 | 11/2017 |
| WO | 2017/201504 A1 | 11/2017 |
| WO | 2017/218734 A1 | 12/2017 |
| WO | 2018/005511 A1 | 1/2018 |
| WO | 2018/106569 A1 | 6/2018 |
| WO | 2018/200800 A1 | 11/2018 |
| WO | 2019/023259 A2 | 1/2019 |
| WO | 2019/023280 A1 | 1/2019 |
| WO | 2019/035071 A1 | 2/2019 |
| WO | 2019/133606 A1 | 7/2019 |
| WO | 2019/133608 A1 | 7/2019 |
| WO | 2019/136218 A1 | 7/2019 |
| WO | 2019/143960 A1 | 7/2019 |
| WO | 2019/181612 A1 | 9/2019 |
| WO | 2019/234133 A1 | 12/2019 |

OTHER PUBLICATIONS

Hobbs, E. P., "Investor Relations Update: Tissue Ablation via Irreversible Electroporation (IRE)," Powerpoint (2004), 16 pages.
International Search Report and Written Opinion received for PCT Patent Application No. PCT/US2021/042586, mailed on Oct. 27, 2021, 09 pages.
Lavee, J. et al., "A Novel Nonthermal Energy Source for Surgical Epicardial Atrial Ablation: Irreversible Electroporation," The Heart Surgery Forum #2006-1202, 10(2), 2007 [Epub Mar. 2007].
Madhavan, M. et al., "Novel Percutaneous Epicardial Autonomic Modulation in the Canine for Atrial Fibrillation: Results of an Efficacy and Safety Study," Pace, 00:1-11 (2016).
Neven, K. et al., "Epicardial linear electroporation ablation and lesion size," Heart Rhythm, 11:1465-1470 (2014).
Neven, K. et al., "Myocardial Lesion Size After Epicardial Electroporation Catheter Ablation After Subxiphoid Puncture," Circ Arrhythm Electrophysiol., 7(4):728-733 (2014).
Neven, K. et al., "Safety and Feasibility of Closed Chest Epicardial Catheter Ablation Using Electroporation," Circ Arrhythm Electrophysiol., 7:913-919 (2014).
Van Driel, V.J.H.M. et al., "Low vulnerability of the right phrenic nerve to electroporation ablation," Heart Rhythm, 12:1838-1844 (2015).
Van Driel, V.J.H.M. et al., "Pulmonary Vein Stenosis After Catheter Ablation Electroporation Versus Radiofrequency," Circ Arrhythm Electrophysiol., 7(4):734-738 (2014).
Wittkampf, F.H. et al., "Feasibility of Electroporation for the Creation of Pulmonary Vein Ostial Lesions," J Cardiovasc Electrophysiol, 22(3):302-309 (Mar. 2011).
Wittkampf, F.H. et al., "Myocardial Lesion Depth With Circular Electroporation Ablation," Circ. Arrhythm Electrophysiol., 5(3):581-586 (2012).

\* cited by examiner

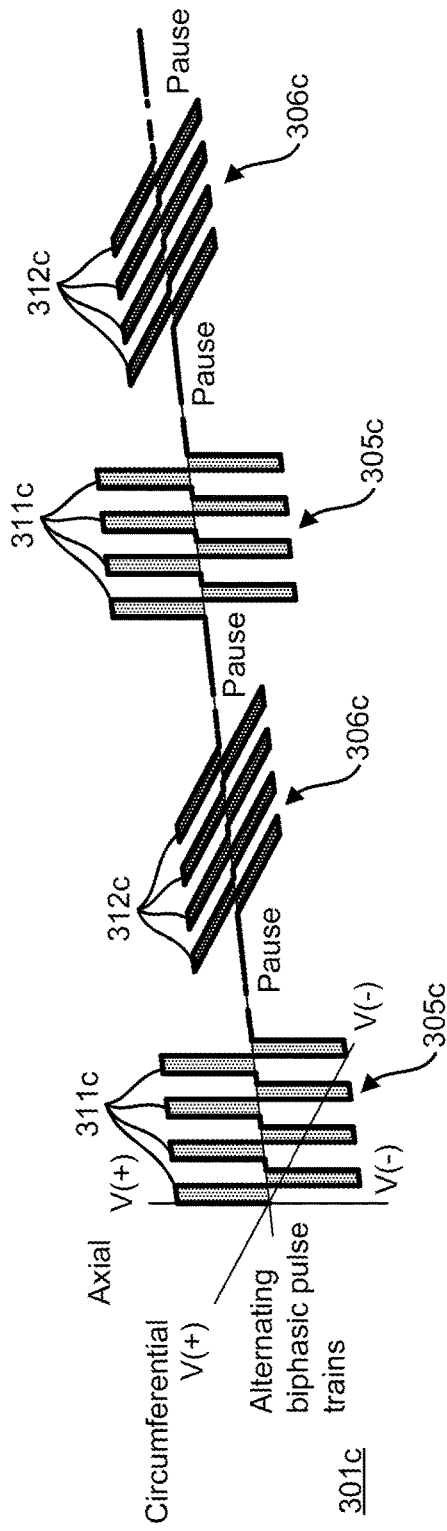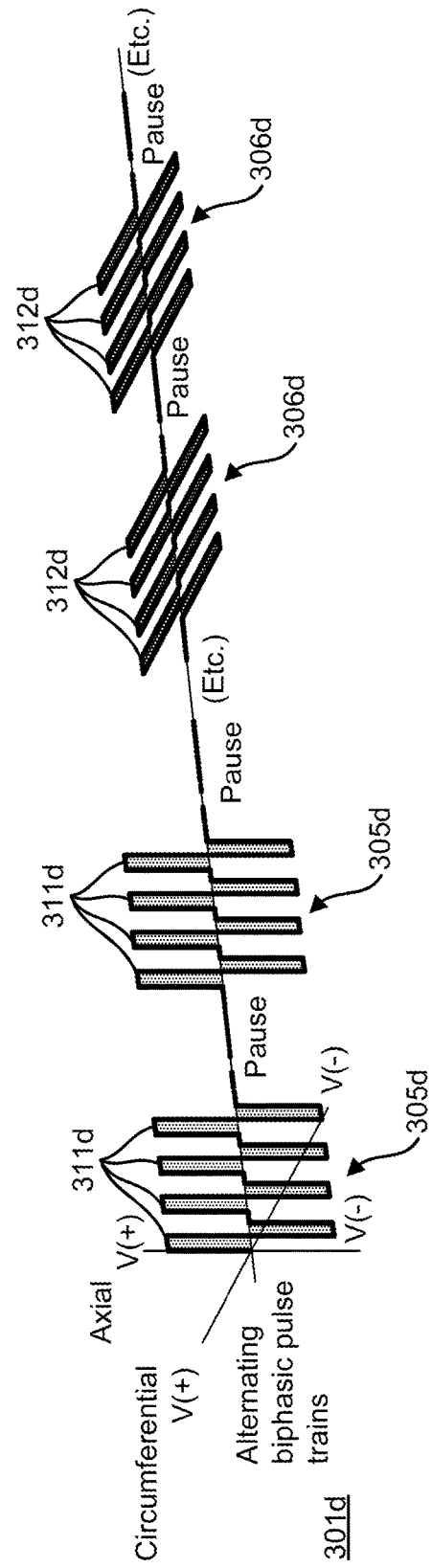
FIG. 3C
FIG. 3D

ELECTRIC FIELD APPLICATION FOR SINGLE SHOT CARDIAC ABLATION BY IRREVERSIBLE ELECTROPORATION

CROSS REFERENCE TO RELATED APPLICATION

This application claims priority to Provisional Application No. 63/056,017, filed Jul. 24, 2020, which is herein incorporated by reference in its entirety.

TECHNICAL FIELD

The present disclosure relates to medical apparatus, systems, and methods for ablating tissue in a patient. More specifically, the present disclosure relates to medical apparatus, systems, and methods for ablation of tissue by electroporation.

BACKGROUND

Ablation procedures are used to treat many different conditions in patients. Ablation may be used to treat cardiac arrhythmias, benign tumors, cancerous tumors, and to control bleeding during surgery. Usually, ablation is accomplished through thermal ablation techniques including radiofrequency (RF) ablation and cryoablation. In RF ablation, a probe is inserted into the patient and radio frequency waves are transmitted through the probe to the surrounding tissue. The radio frequency waves generate heat, which destroys surrounding tissue and cauterizes blood vessels. In cryoablation, a hollow needle or cryoprobe is inserted into the patient and cold, thermally conductive fluid is circulated through the probe to freeze and kill the surrounding tissue. RF ablation and cryoablation techniques indiscriminately kill tissue through cell necrosis, which may damage or kill otherwise healthy tissue, such as tissue in the esophagus, phrenic nerve cells, and tissue in the coronary arteries.

Another ablation technique uses electroporation. In electroporation, or electro-permeabilization, an electric field is applied to cells to increase the permeability of the cell membrane. The electroporation may be reversible or irreversible, depending on the strength of the electric field. If the electroporation is reversible, the increased permeability of the cell membrane may be used to introduce chemicals, drugs, and/or deoxyribonucleic acid (DNA) into the cell, prior to the cell healing and recovering. If the electroporation is irreversible, the affected cells are killed through apoptosis.

Irreversible electroporation may be used as a nonthermal ablation technique. In irreversible electroporation, trains of short, high voltage pulses are used to generate electric fields that are strong enough to kill cells through apoptosis. In ablation of cardiac tissue, irreversible electroporation may be a safe and effective alternative to the indiscriminate killing of thermal ablation techniques, such as RF ablation and cryoablation. Irreversible electroporation may be used to kill targeted tissue, such as myocardium tissue, by using an electric field strength and duration that kills the targeted tissue but does not permanently damage other cells or tissue, such as non-targeted myocardium tissue, red blood cells, vascular smooth muscle tissue, endothelium tissue, and nerve cells. But the effectiveness of electroporation depends on exposing targeted tissue to a critical electric field strength, which depends on electrode geometry. This much is true because irreversible electroporation effectiveness depends on cell geometry and/or orientation relative to the generated electric field. And often, electrode geometry is such that an electric field produced by the electrodes has limited (e.g., single) orientations.

SUMMARY

In Example 1, an electroporation ablation system for treating target tissue, the electroporation ablation system comprising an ablation catheter and an electroporation generator. The ablation catheter includes a shaft defining a longitudinal axis of the ablation catheter, and an electroporation electrode arrangement at a distal end of the shaft and including a plurality of electrodes arranged so as to define a plurality of anode-cathode pairs each configured to generate an electric field when an electrical pulse sequence is delivered thereto. The plurality of anode-cathode pairs includes a first anode-cathode pair arranged so as to generate a first electric field having a first orientation relative to the longitudinal axis when a first electrical pulse sequence is delivered thereto, and
a second anode-cathode pair arranged so as to generate a second electric field having a second orientation relative to the longitudinal axis when a second electrical pulse sequence is delivered thereto. The electroporation generator is operatively coupled to the electroporation electrode arrangement and configured to selectively generate and deliver the first electrical pulse sequence to first anode-cathode pair, and the second electrical pulse sequence to the second anode-cathode pair.

In Example 2, the electroporation ablation system of Example 1, wherein the first orientation is generally aligned with the longitudinal axis, and wherein the second orientation is circumferential about the longitudinal axis.

In Example 3, the electroporation ablation system of Example 1, wherein the first orientation is generally aligned with the longitudinal axis, and wherein the second orientation is transverse to the longitudinal axis.

In Example 4, the electroporation ablation system of Example 1, wherein the first orientation is transverse to the longitudinal axis, and the second orientation is generally circumferential about the longitudinal axis.

In Example 5, the electroporation ablation system of any of Examples 1-4, wherein each of the first and second pulse sequences comprises a plurality of direct current (DC) pulses.

In Example 6, the electroporation ablation system of Example 5, wherein the DC pulses are monophasic pulses, biphasic pulses, or triphasic pulses.

In Example 7, the electroporation ablation system of Example 6, wherein the electroporation generator is configured to generate the DC pulses of each electrical pulse sequence separated by an inter-pulse delay, and wherein at least some of the DC pulses of the second electrical pulse sequence are delivered during a respective inter-pulse delay of the first electrical pulse sequence.

In Example 8, the electroporation system of Example 6, wherein the electroporation generator is configured to generate a plurality of electrical pulse sequence sets having a pause therebetween, wherein each electrical pulse sequence set comprises the first electrical pulse sequence and the second electrical pulse sequence.

In Example 9, the electroporation ablation system of Example 6, wherein DC pulses are biphasic pulses, and the electroporation ablation generator is configured to alternate between delivering the first electrical pulse sequence to the first anode-cathode pair, and the second electrical pulse sequence to the second anode-cathode pair.

In Example 10, the electroporation ablation system of Example 6, wherein each of the DC pulses is a triphasic pulse defined by a first phase having a first phase voltage and a first phase length, a second phase having a second phase voltage and a second phase length, and a third phase having a third phase voltage and a third phase length, wherein the first and third phases have the same polarity and the second phase has an opposite polarity thereto.

In Example 11, the electroporation ablation system of Example 10, wherein the first phase voltage, the first phase length, the second phase voltage, the second phase length, the third phase voltage and the third phase length are selected such that each DC pulse is charge-and-energy balanced.

In Example 12, the electroporation ablation system of Example 11, the first, second and third phase voltages are equal to each other, and wherein the first and third phase lengths are equal to one another and have a duration of one-half of the second phase length.

In Example 13, the electroporation ablation system of Example 11, wherein the first and third phase voltages and phase lengths are equal to each other, and are different from the second phase voltage and the second phase length, respectively.

In Example 14, the electroporation ablation system of Example 10, wherein the first, second and third phase lengths and the first, second and third phase voltages are selected such that each DC pulse is charge imbalanced so as to encourage electrolysis of the target tissue.

In Example 15, the electroporation ablation system of Example 5, wherein each DC pulse of the first electrical pulse sequence has a first voltage and a first pulse length selected to ablate the target tissue by irreversible electroporation, and wherein each DC pulse of the second pulse sequence has a second voltage and a second pulse length selected to create electrolytic byproducts at the target tissue proximate the second anode-cathode pair.

In Example 16, an electroporation ablation system for treating target tissue, the electroporation ablation system comprising an ablation catheter and an electroporation generator. The ablation catheter includes
   a handle, a shaft having a distal end and defining a longitudinal axis of the ablation catheter, and an electroporation electrode arrangement at the distal end of the shaft and including a plurality of electrodes spatially arranged so as generate a plurality of electric fields when an electrical pulse sequence is delivered to selected pairs of the electrodes, the plurality of electric fields including a first electric field having a first orientation relative to the longitudinal axis, and second electric field having a second orientation relative to the longitudinal axis. The electroporation generator is operatively coupled to the electroporation electrode arrangement and configured to selectively generate and deliver the electrical pulse sequences to each selected pair of electrodes.

In Example 17, the electroporation ablation system of Example 16, wherein the first orientation is generally aligned with the longitudinal axis, and wherein the second orientation is circumferential about the longitudinal axis.

In Example 18, the electroporation ablation system of Example 16, wherein the first orientation is generally aligned with the longitudinal axis, and wherein the second orientation is transverse to the longitudinal axis.

In Example 19, the electroporation ablation system of Example 16, wherein the first orientation is transverse to the longitudinal axis, and the second orientation is generally circumferential about the longitudinal axis.

In Example 20, the electroporation ablation system of Example 16, wherein each of the plurality of electrical pulse sequences comprises a plurality of direct current (DC) pulses.

In Example 21, the electroporation ablation system of Example 20, wherein the DC pulses are monophasic pulses, biphasic pulses, or triphasic pulses.

In Example 22, the electroporation ablation system of Example 20, wherein the electroporation generator is configured to generate the DC pulses of each pulse sequence separated by an inter-pulse delay, and wherein at least some of the DC pulses of a first electrical pulse sequence are delivered during a respective inter-pulse delay of a second electrical pulse sequence.

In Example 23, the electroporation system of Example 16, wherein the electroporation generator is configured to generate a plurality of electrical pulse sequence sets having a pause therebetween, wherein each electrical pulse sequence set comprises a plurality of electrical pulse sequences.

In Example 24, the electroporation ablation system of Example 20, wherein the electroporation generator is configured to generate the DC pulses of each electrical pulse sequence separated by an inter-pulse delay, and wherein at least some of the DC pulses of the second electrical pulse sequence are delivered during a respective inter-pulse delay of the first electrical pulse sequence.

In Example 25, the electroporation ablation system of Example 20, wherein DC pulses are biphasic pulses, and the electroporation ablation generator is configured to alternate between delivering the first electrical pulse sequence to the first anode-cathode pair, and the second electrical pulse sequence to the second anode-cathode pair.

In Example 26, an electroporation ablation system for treating target tissue, the electroporation ablation system comprising an ablation catheter including a handle, a shaft having a distal end and defining a longitudinal axis of the ablation catheter, and an electroporation electrode arrangement at the distal end of the shaft and including a plurality of electrodes arranged so as to define a plurality of electrode pairs each configured to generate an electric field when an electrical pulse sequence is delivered thereto, the plurality of electrode pairs including a first electrode pair arranged so as to generate a first electric field having a first orientation relative to the longitudinal axis when a first electrical pulse sequence is delivered thereto; and
   a second electrode pair arranged so as to generate a second electric field having a second orientation relative to the longitudinal axis when a second electrical pulse sequence is delivered thereto. The electroporation generator is operatively coupled to the electroporation electrode arrangement and configured to selectively generate and deliver the first electrical pulse sequence to first electrode pair, and the second electrical pulse sequence to the second electrode pair.

In Example 27, the electroporation ablation system of Example 26, wherein the first orientation is generally aligned with the longitudinal axis, and wherein the second orientation is circumferential about the longitudinal axis.

In Example 28, the electroporation ablation system of Example 26, wherein the first orientation is generally aligned with the longitudinal axis, and wherein the second orientation is transverse to the longitudinal axis.

In Example 29, the electroporation ablation system of Example 26, wherein the first orientation is transverse to the longitudinal axis, and the second orientation is generally circumferential about the longitudinal axis.

In Example 30, the electroporation ablation system of Example 26, wherein the first and second electrical pulse sequences each comprise a plurality of biphasic DC pulses, and the wherein the electroporation ablation generator is configured to alternate between delivering the first electrical pulse sequence to the first electrode pair, and the second electrical pulse sequence to the second electrode pair.

In Example 31, a method of generating and delivering a signal to electrodes in an electroporation ablation system, the method comprising delivering a first electrical pulse sequence to a first electrode pair of an electroporation catheter having a longitudinal axis so as to generate a first electric field having a first orientation relative to the longitudinal axis, and delivering a second electrical pulse sequence to a second electrode pair of the electroporation catheter so as to generate a second electric field having a second orientation relative to the longitudinal axis.

In Example 32, the method of Example 31, wherein delivering the first electrical pulse sequence to the first electrode pair and delivering the second electrical pulse sequence to the second electrode pair includes alternatingly delivering, over a time period, the first electrical pulse sequence to the first electrode pair and delivering the second electrical pulse sequence to the second electrode pair to produce a dynamically gyrating electric field that comprises a changing pattern over the time period.

In Example 33, the method of Example 32, wherein the first orientation is generally aligned with the longitudinal axis, and wherein the second orientation is circumferential about the longitudinal axis.

In Example 34, the method of Example 32, wherein the first orientation is generally aligned with the longitudinal axis, and wherein the second orientation is transverse to the longitudinal axis.

In Example 35, the method of Example 32, wherein the first orientation is transverse to the longitudinal axis, and the second orientation is generally circumferential about the longitudinal axis.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

BRIEF DESCRIPTION OF THE DRAWINGS

FIGS. 3C-3D are diagrams schematically illustrating exemplary biphasic electrical pulse sequences to be delivered to electrodes in an electrode arrangement according to embodiments of subject matter of the disclosure.

Figure 1:
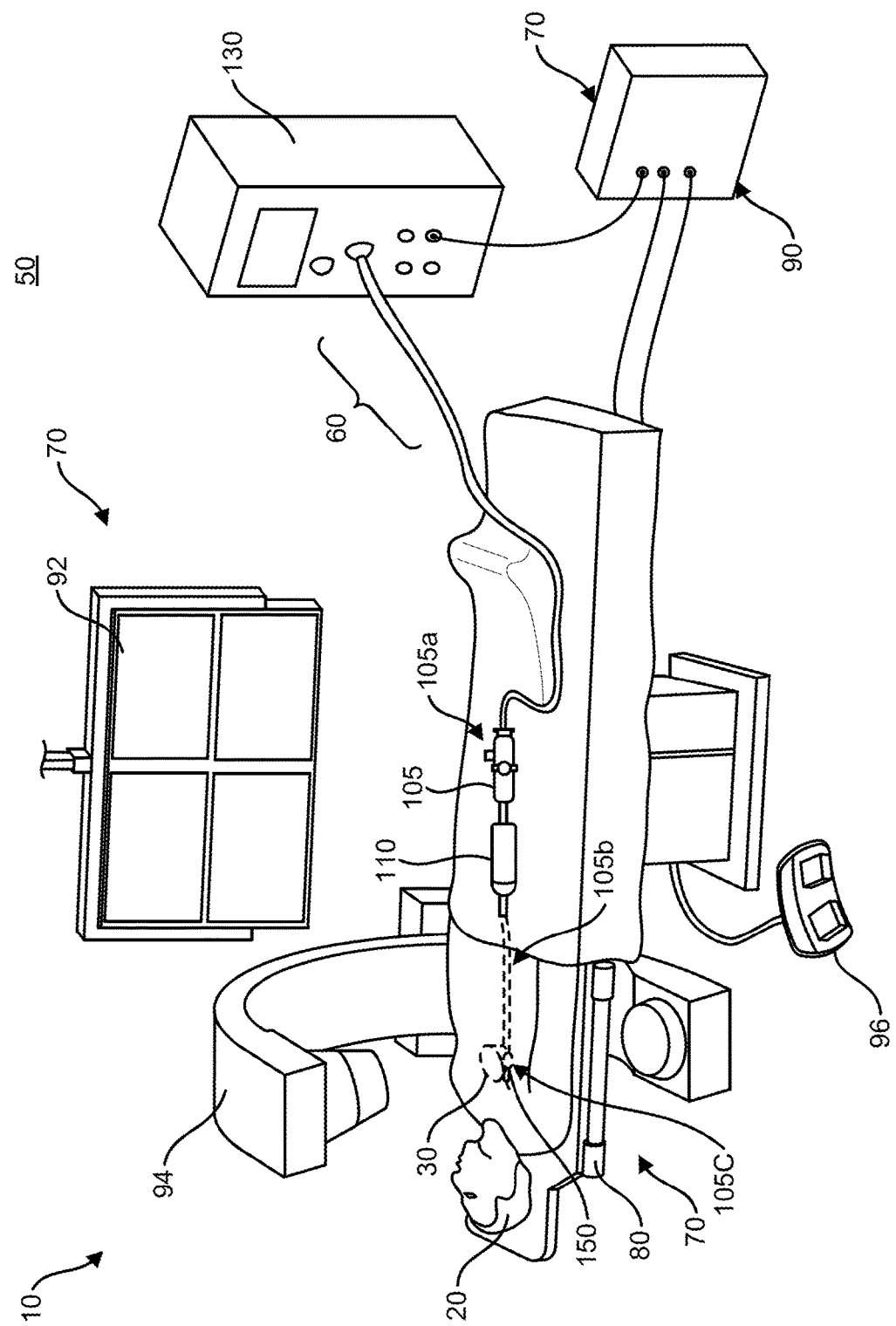
FIG. 1 is a diagram illustrating an exemplary clinical setting for treating a patient and for treating a heart of the patient, using an electrophysiology system, in accordance with embodiments of the subject matter of the disclosure.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

The following detailed description is exemplary in nature and is not intended to limit the scope, applicability, or configuration of the invention in any way. Rather, the following description provides some practical illustrations for implementing exemplary embodiments of the present invention. Examples of constructions, materials, and/or dimensions are provided for selected elements. Those skilled in the art will recognize that many of the noted examples have a variety of suitable alternatives.

FIG. 1 is a diagram illustrating an exemplary clinical setting 10 for treating a patient 20, and for treating a heart 30 of the patient 20, using an electrophysiology system 50, in accordance with embodiments of the subject matter of the disclosure. The electrophysiology system 50 includes an electroporation catheter system 60 and an electro-anatomical mapping (EAM) system 70, which includes a localization field generator 80, a mapping and navigation controller 90, and a display 92. Also, the clinical setting 10 includes additional equipment such as imaging equipment 94 (represented by the C-arm) and various controller elements, such as a foot controller 96, configured to allow an operator to control various aspects of the electrophysiology system 50. As will be appreciated by the skilled artisan, the clinical setting 10 may have other components and arrangements of components that are not shown in FIG. 1.

The electroporation catheter system 60 includes an electroporation catheter 105, an introducer sheath 110, and an electroporation generator 130. Additionally, the electroporation catheter system 60 includes various connecting elements (e.g., cables, umbilicals, and the like) that operate to functionally connect the components of the electroporation catheter system 60 to one another and to the components of the EAM system 70. This arrangement of connecting elements is not of critical importance to the present disclosure, and one skilled in the art will recognize that the various components described herein may be interconnected in a variety of ways.

In embodiments, the electroporation catheter system 60 is configured to deliver electric field energy to targeted tissue in the patient's heart 30 to create tissue apoptosis, rendering the tissue incapable of conducting electrical signals. The electroporation generator 130 is configured to control functional aspects of the electroporation catheter system 60. In embodiments, the electroporation generator 130 is operable as an electroporation pulse generator for generating and supplying pulse sequences to the electroporation catheter 105, as described in greater detail herein In embodiments, the electroporation generator 130 includes one or more controllers, microprocessors, and/or computers that execute code out of memory to control and/or perform the functional aspects of the electroporation catheter system 60. In embodiments, the memory may be part of the one or more controllers, microprocessors, and/or computers, and/or part of memory capacity accessible through a network, such as the world wide web.

In embodiments, the introducer sheath 110 is operable to provide a delivery conduit through which the electroporation catheter 105 may be deployed to the specific target sites within the patient's heart 30. It will be appreciated, however, that the introducer sheath 110 is illustrated and described herein to provide context to the overall electrophysiology system 50, but it is not critical to the novel aspects of the various embodiments described herein.

The EAM system 70 is operable to track the location of the various functional components of the electroporation catheter system 60, and to generate high-fidelity three-dimensional anatomical and electro-anatomical maps of the cardiac chambers of interest. In embodiments, the EAM system 70 may be the RHYTHMIA™ HDx mapping system marketed by Boston Scientific Corporation. Also, in embodiments, the mapping and navigation controller 90 of the EAM system 70 includes one or more controllers, microprocessors, and/or computers that execute code out of memory to control and/or perform functional aspects of the EAM system 70, where the memory, in embodiments, may be part of the one or more controllers, microprocessors, and/or computers, and/or part of memory capacity accessible through a network, such as the world wide web.

As will be appreciated by the skilled artisan, the depiction of the electrophysiology system 50 shown in FIG. 1 is intended to provide a general overview of the various components of the system 50 and is not in any way intended to imply that the disclosure is limited to any set of components or arrangement of the components. For example, the skilled artisan will readily recognize that additional hardware components, e.g., breakout boxes, workstations, and the like, may and likely will be included in the electrophysiology system 50.

The EAM system 70 generates a localization field, via the field generator 80, to define a localization volume about the heart 30, and one or more location sensors or sensing elements on the tracked device(s), e.g., the electroporation catheter 105, generate an output that may be processed by the mapping and navigation controller 90 to track the location of the sensor, and consequently, the corresponding device, within the localization volume. In the illustrated embodiment, the device tracking is accomplished using magnetic tracking techniques, whereby the field generator 80 is a magnetic field generator that generates a magnetic field defining the localization volume, and the location sensors on the tracked devices are magnetic field sensors.

In other embodiments, impedance tracking methodologies may be employed to track the locations of the various devices. In such embodiments, the localization field is an electric field generated, for example, by an external field generator arrangement, e.g., surface electrodes, by intra-body or intra-cardiac devices, e.g., an intracardiac catheter, or both. In these embodiments, the location sensing elements may constitute electrodes on the tracked devices that generate outputs received and processed by the mapping and navigation controller 90 to track the location of the various location sensing electrodes within the localization volume.

In embodiments, the EAM system 70 is equipped for both magnetic and impedance tracking capabilities. In such embodiments, impedance tracking accuracy can, in some instances, be enhanced by first creating a map of the electric field induced by the electric field generator within the cardiac chamber of interest using a probe equipped with a magnetic location sensor, as is possible using the aforementioned RHYTHMIA HDx™ mapping system. One exemplary probe is the INTELLAMAP ORION™ mapping catheter marketed by Boston Scientific Corporation.

Regardless of the tracking methodology employed, the EAM system 70 utilizes the location information for the various tracked devices, along with cardiac electrical activity acquired by, for example, the electroporation catheter 105 or another catheter or probe equipped with sensing electrodes, to generate, and display via the display 92, detailed three-dimensional geometric anatomical maps or representations of the cardiac chambers as well as electro-anatomical maps in which cardiac electrical activity of interest is superimposed on the geometric anatomical maps. Furthermore, the EAM system 70 may generate a graphical representation of the various tracked devices within the geometric anatomical map and/or the electro-anatomical map.

While the EAM system 70 is shown in combination with the electroporation catheter system 60 to provide a comprehensive depiction of an exemplary clinical setting 10, the EAM system 70 is not critical to the operation and functionality of the electroporation catheter system 60. That is, in embodiments, the electroporation catheter system 60 can be employed independently of the EAM system 70 or any comparable electro-anatomical mapping system.

In the illustrated embodiment, the electroporation catheter 105 includes a handle 105*a*, a shaft 105*b*, and an electroporation electrode arrangement 150, which is described further hereinafter. The handle 105*a* is configured to be operated by a user to position the electroporation electrode arrangement 150 at the desired anatomical location. The shaft 105*b* has a distal end 105*c* and generally defines a longitudinal axis of the electroporation catheter 105. As shown, the electroporation electrode arrangement 150 is located at or proximate the distal end 105c of the shaft 105b. In embodiments, the electroporation electrode arrangement 150 is electrically coupled to the electroporation generator 130, so as to receive electrical pulse sequences or pulse trains, thereby selectively generating electrical fields for ablating the target tissue by irreversible electroporation.

As described above and also in greater detail elsewhere herein, the electroporation catheter system 60 is operable to generate a multidirectional electric field for ablating target tissue via irreversible electroporation. Such procedures include single-shot ablation procedures, e.g., pulmonary vein isolation (PVI) procedures as well as focal cardiac ablation procedures.

Figure 2A:
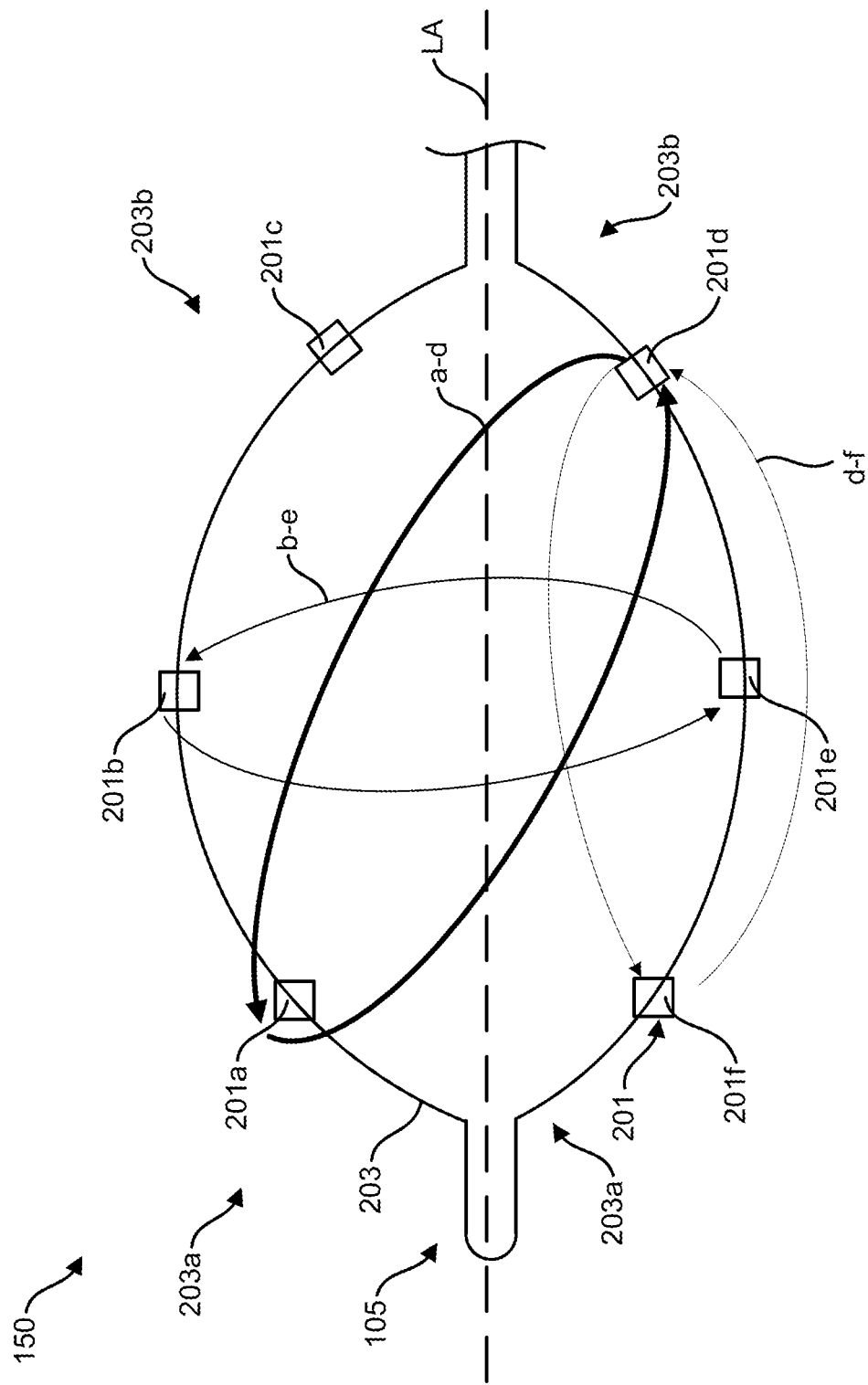
FIG. 2A is a diagram illustrating a distal end of a shaft included in a catheter and interactions between electrode pairs, in accordance with embodiments of the subject matter of the disclosure.
Figure 2C:
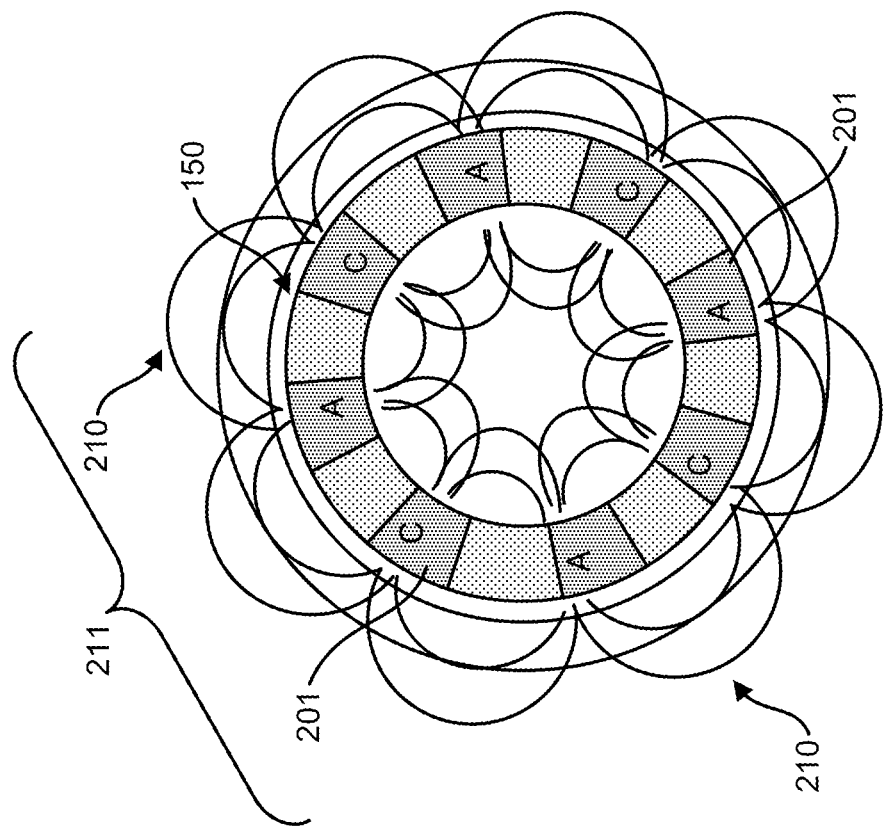
FIG. 2C is a diagram illustrating circumferential electric fields generated by interactions between electrode pairs in the catheter, in accordance with embodiments of the subject matter of the disclosure.
Figure 2B:
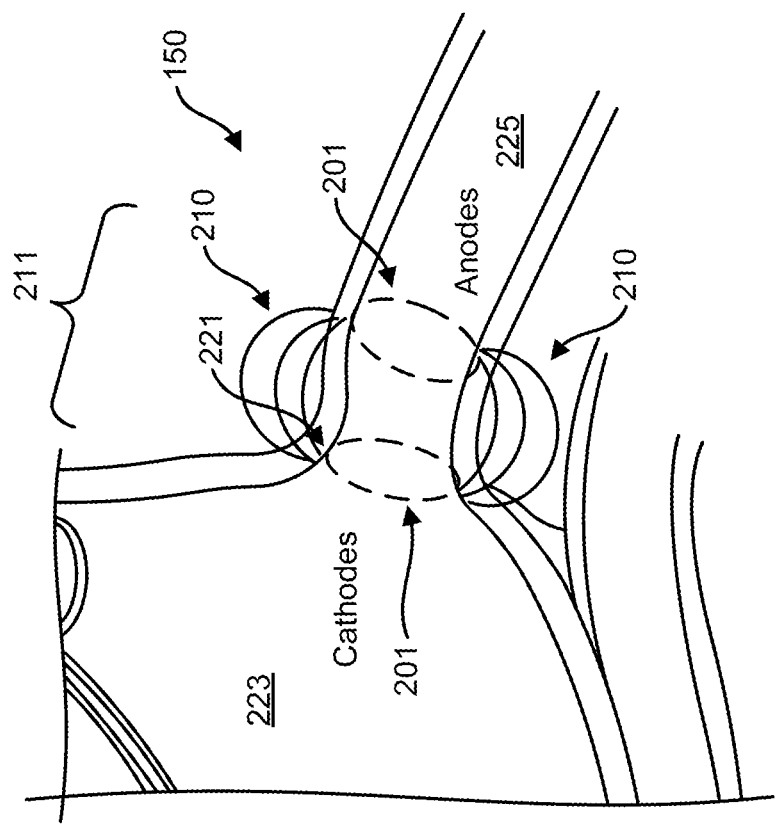
FIG. 2B is a diagram illustrating axial electric fields generated by interactions between electrode pairs, in accordance with embodiments of the subject matter of the disclosure.

FIGS. 2A-2C show features of the electroporation catheter 105 that includes the electroporation electrode arrangement 150 according to embodiments. In the illustrated embodiment in FIG. 2A, the electroporation electrode arrangement 150 includes a plurality of electrodes 201a, 201b, 201c, 201d, 201e, and 201f arranged in a three-dimensional electrode array, such that respective ones of the electrodes 201a, 201b, 201c, 201d, 201e, and 201f are spaced from one another axially (i.e., in the direction of the longitudinal axis LA), circumferentially about the longitudinal axis LA and/or radially relative to the longitudinal axis LA. In embodiments, the electrodes 201a, 201b, 201c, 201d, 201e, and 201f are each individually, selectively addressable via the electroporation generator 130 (FIG. 1) so as to define a plurality of anode-cathode electrode pairs, each capable of receiving an electrical pulse sequence from the electroporation generator 130 and, consequently, creating an electric field capable of selectively ablating target tissue via irreversible electroporation. FIG. 2A schematically illustrates interactions (e.g., current flows forming electric fields) between electrode pairs formed between electrodes 201 (e.g., 201a, 201b, 201c, 201d, 201e, and 201f) included in the electroporation catheter 105. In this figure, interactions are shown as paired arrows (e.g., a-d, b-e, and d-f) indicating current flows between electrodes 201. And electrode pairs (e.g., 201a and 201d, 201b and 201e, and 201d and 201f) are shown with their respective current flows (e.g., a-d, b-e, and d-f) labeled.

FIG. 2B is a diagram illustrating electric fields 210 generated by interactions between electrode pairs in the electroporation catheter 105. In this figure, axially oriented electric fields 210 are shown positioned at an ostium 221 between the left atrium 223 and the left inferior pulmonary vein 225. In embodiments, the axially oriented electric fields 210 are produced by delivering electrical pulses to axially spaced anodes and cathodes.

FIG. 2C is also a diagram illustrating electric fields 210 generated by interactions between electrode pairs in the electroporation catheter 105. But here, the electric fields 210 are circumferentially oriented. In embodiments, the circumferentially oriented electric fields 210 are produced by delivering electrical pulses to circumferentially spaced anodes ("A") and cathodes ("C").

Between FIGS. 2A-2C, it is apparent that multiple electric fields 210 may be generated simultaneously and/or sequentially and in axial and circumferential orientations. For example, in embodiments, axially and circumferentially oriented electric fields 210 can be generated non-simultaneously in a pre-defined sequence by selectively controlling the timing of the delivery of the electric pulses to the respective electrodes 201. In addition, it is understood that intermittently generated electric fields 210 caused by staggered interactions between sets of electrode pairs and electric field orientations other than axial and circumferential are not beyond the scope of this disclosure and are indeed described in detail hereinafter.

As may be seen in FIG. 2A, the electroporation electrode arrangement 150 may include a plurality of individually addressable electrodes 201 (e.g., anodes or cathodes) arranged so as to selectively define a plurality of electrode pairs (e.g., anode-cathode pairs). Each anode-cathode pair may be configured to generate an electric field when a pulse sequence is delivered thereto. The plurality of anode-cathode pairs may include at least two of a first anode-cathode pair, a second anode-cathode pair, and a third anode-cathode pair. The first anode-cathode pair may be arranged so as to generate a first electric field oriented generally circumferentially relative to the longitudinal axis when a first pulse sequence is delivered thereto. The second anode-cathode pair may be arranged so as to generate a second electric field oriented generally in a same direction as the longitudinal axis when a second pulse sequence is delivered thereto. The third anode-cathode pair may be arranged so as to generate a third electric field oriented generally transverse to the longitudinal axis when a third pulse sequence is delivered thereto. In embodiments, any combination of the first, second, and third pulse sequences may be delivered simultaneously or intermittently and may take a variety of forms as described hereinafter.

In embodiments, the electroporation electrode arrangement 150 may be configured so as to structurally arrange the electrodes 201a, 201b, 201c, 201d, 201e, and 201f into a distally-located first region and a more proximally-located second region. As such, electrode pairs may be formed across various electrodes 201 in the electroporation electrode arrangement 150 between first and second regions. For example, the electrodes 201d and 201f may be configured to form an electrode pair. Similarly, the electrodes 201a and 201d or electrodes 201b and 201e or the combination thereof may be selected to form respective electrode pairs. Thus, the electrode pairs may comprise axially spaced electrodes, transversely spaced electrodes, or circumferentially spaced electrodes. Additionally, in embodiments, a given electrode (e.g., 201d) may serve as a common electrode in at least two electrode pairs to generate electric fields 210.

FIG. 2B shows a diagram of exemplary electric fields 210 that may be generated by the electroporation electrode arrangement 150. The electroporation electrode arrangement 150 may be configured to generate a multidirectional electric field 210 when at least one pulse sequence is delivered thereto. The multidirectional electric field 210 may include at least two of the following directions relative to the longitudinal axis: generally axial, circumferential, and transverse. As used herein, transverse may mean at any non-parallel angle relative to the longitudinal axis. As described elsewhere herein, the electroporation electrode arrangement 150 may be configured to operatively couple to an electroporation generator that is configured to generate the at least one pulse sequence. The electroporation electrode arrangement 150 may be configured to receive the at least one pulse sequence from the electroporation generator. Thus, the electroporation electrode arrangement 150 and the electroporation generator may be in operative communication with each other. In this disclosure, such communication may be used to generate electric fields 210 that are at least substantially gapless.

Undesired gaps in electric fields 210 generated by the electroporation electrode arrangement 150 may be limited or at least substantially eliminated. Such gaps may potentially lead to lesion gaps and therefore require multiple repositions of a catheter, for example. Overlapping electric fields 210 may at least substantially limit the number of such gaps. In embodiments, at least some the electric fields 210 generated in the first pulse sequence set may overlap at least partially with each other. For example, adjacent electric fields 210 (e.g., axial, transverse, and/or circumferential) in a combined electric field 211 may intersect one another so that there are limited to no gaps in the combined electric field 211. Overlapping may occur at or near the periphery of adjacent electric fields 210 or may occur over a preponderance or majority of one or more adjacent electric fields 210. In this disclosure, adjacent means neighboring electrodes 201 or electrodes 201 otherwise near each other. The electroporation generator may be configured to generate pulse sequences used in generating overlapping electric fields.

The configuration of the electroporation electrode arrangement 150 in the various embodiments may take on any form, whether now known or later developed, suitable for a three-dimensional electrode structure. In exemplary embodiments, the electroporation electrode arrangement 150 may be in the form of a splined basket catheter, with respective electrodes 201a, 201b, 201c, 201d, 201e, and 201f positioned on a plurality of splines in any manner known in the art. In embodiments, the electroporation electrode arrangement 150 can be formed on an expandable balloon, e.g., with electrodes formed on flexible circuit branches or individual traces disposed on the balloon surface. In other embodiments, the electroporation electrode arrangement 150 may be in the form of an expandable mesh. In short, the particular structure used to form the electroporation electrode arrangement 150 is not critical to the embodiments of the present disclosure.

FIGS. 3A-3I show a variety of electrical pulse sequences that may be delivered to the electroporation electrode arrangement, e.g., by the electroporation generator, in accordance with embodiments of the subject matter of the disclosure. As can be seen in FIGS. 3A-3I and as described herein, the various exemplary pulse sequences that can be delivered to the plurality of anode-cathode pairs described above may include monophasic pulses biphasic pulses, triphasic pulses, and quadphasic pulses. Time-based characteristics of each pulse include an orientation (e.g., axial, circumferential, or transverse) and a polarity (e.g., positive (+) or negative (−)) as indicated on the axes.

Figure 3A:
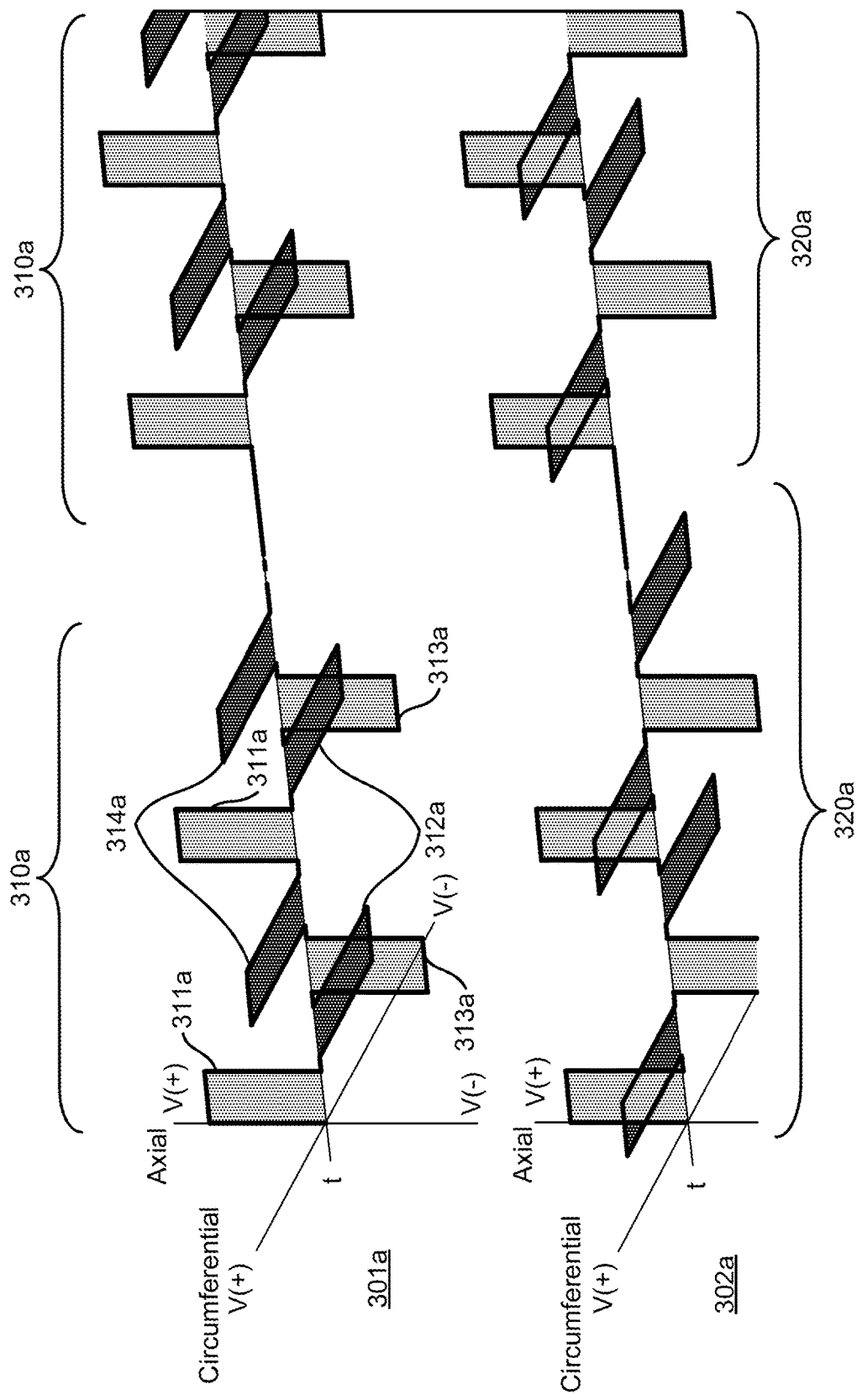
FIG. 3A is a diagram illustrating two pulse sequence series that include two pulse sequence sets having pulse sequences with interlaced, monophasic pulses to be delivered to electrodes in an electroporation electrode arrangement of the catheter, in accordance with embodiments of the subject matter of the disclosure.

FIG. 3A is a diagram illustrating two pulse sequence series 301a, 302a each having two pulse sequence sets 310a, 320a therein. As shown, the pulse sequence set 310a is comprised of monophasic direct current (DC) electrical pulses 311a, 312a, 313a and 314a. In the illustrated embodiment, the electrical pulses 311a, 313a are delivered to anode-cathode pairs oriented generally axially relative to the longitudinal axis of the electroporation catheter, whereas the electrical pulses 312a, 314a are delivered to anode-cathode pairs arranged circumferentially relative to the longitudinal axis. As illustrated, adjacent axially-directed electrical pulses 311a, 313a are monophasic DC pulses separated in time by a predetermined inter-pulse delay, and have an opposite polarity. Similarly, adjacent circumferentially-directed electrical pulses 312a, 314a are monophasic DC pulses separated in time by a predetermined inter-pulse delay, and have opposite polarity. It will be appreciated that in embodiments, the electrical pulses 311a and 313a may have the same (e.g., positive) polarity, and similarly, the electrical pulses 312a and 314a may also have the same polarity. As shown, a series of the electrical pulses 311a, 313a, 312a and 314a are grouped into two electrical pulse sequence sets 310a separated in time by a pause of predetermined length. In the illustrated embodiment, respective circumferentially-directed electrical pulses 312a, 314a are generated and delivered during an inter-pulse delay between adjacent axially-directed electrical pulses 311a, 313a.

In the illustrated embodiment, the pulse sequence series 302a and corresponding pulse sequence sets 320a differ from the pulse sequence series 301a and pulse sequence sets 310a in that the electrical pulses 312a, 314a are reversed in polarity.

With further reference to FIG. 3A, interlacing pulses within a pulse sequence set (e.g., 310a, 320a) may be accomplished using delays in pulse sequences within the pulse sequence set. As described elsewhere herein, the plurality of pulse sequence sets may have a first pulse sequence set 310a that includes both a first generated pulse sequence and a second generated pulse sequence. And each of the first generated pulse sequence (e.g., both pulses 311a) and the second generated pulse sequence (e.g., both pulses 312a) may include a plurality of pulses. The first generated pulse sequence may have a first inter-pulse delay between at least two pulses (e.g., between each pulse 311a in pulse sequence set 310a) therein. The first generated pulse sequence and the second generated pulse sequence may be alternatingly arranged within the first pulse sequence set 310a such that at least one pulse (e.g., the leftmost pulse 312a) in the second generated pulse sequence occurs within the first inter-pulse delay. The second generated pulse sequence may have a second inter-pulse delay between at least two pulses therein (e.g., between each pulse 312a in pulse sequence set 310a). At least one pulse in the first generated pulse sequence (e.g., the rightmost pulse 311a) may occur within the second inter-pulse delay. The plurality of pulse sequence sets may include a second pulse sequence set 310a, 320a that is separate from the first pulse sequence set 310a, 320a (respectively) and that has a pause between the first pulse sequence set and the second pulse sequence set. In embodiments, as shown here, the inter-pulse delay between any two pulse sequences (e.g., between 311a and 312a) may be less than the pause between any two pulse sequence sets. But this disclosure should not be limited to such a configuration because, for instance, in embodiments this inter-pulse delay may be less than or equal to the inter-pulse-set delay if desired. Delays may facilitate forming an interlaced pulse sequence set 310a and/or timing between pulse sequences. As one skilled in the art would appreciate, these concepts may extend across any number of pulses sequences or post sequence sets and any type of pulse.

It will be appreciated that although FIG. 3A depicts electrical pulses for delivery to axially and circumferentially-oriented electrode pairs, in other embodiments, one of these orientations may be substituted by transversely-oriented electrode pairs.

Figure 3B:
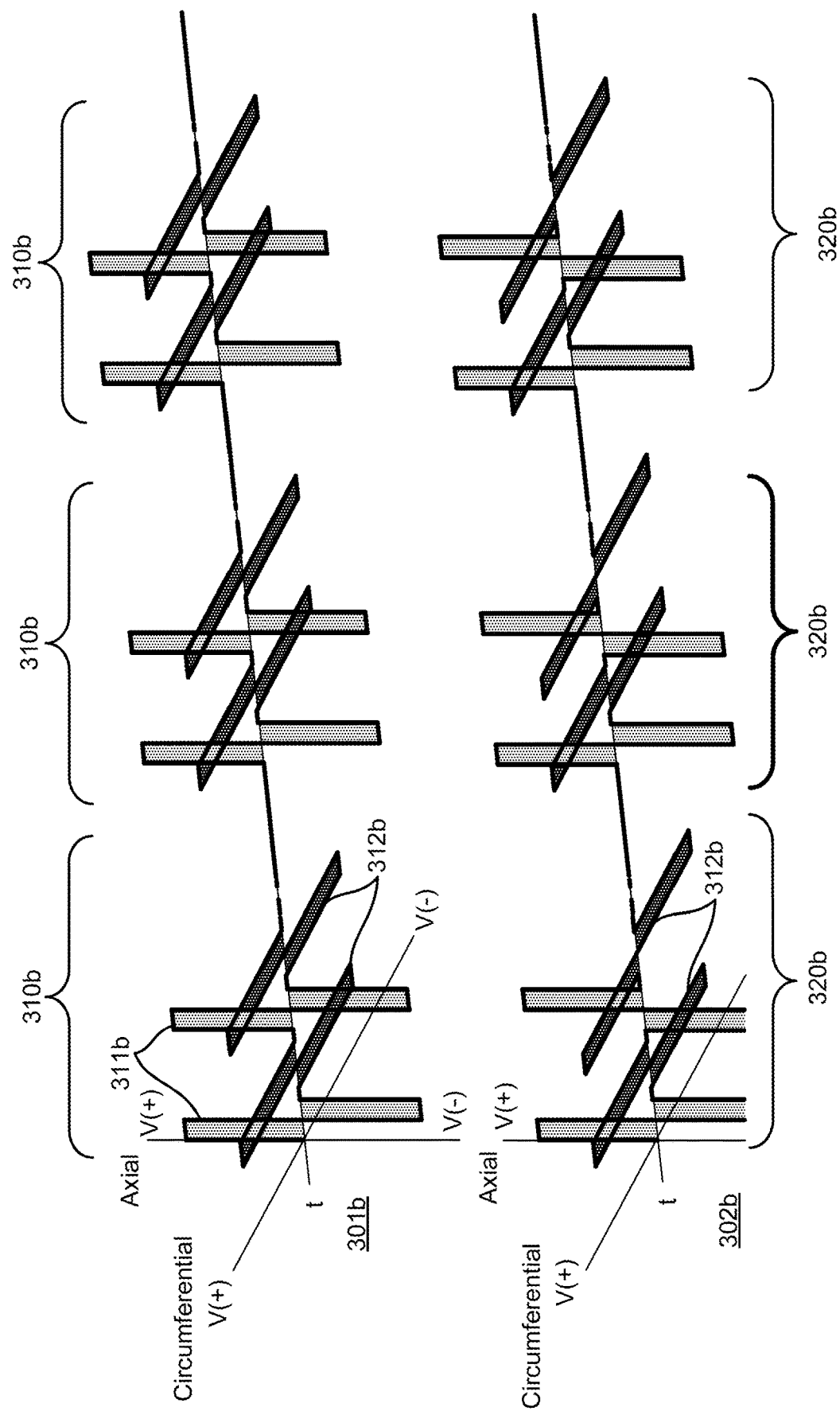
FIG. 3B is a diagram illustrating two pulse sequence series that include two pulse sequence sets having pulse sequences with interlaced, biphasic pulses to be delivered to electrodes in an electroporation electrode arrangement of the catheter, in accordance with embodiments of the subject matter of the disclosure.

FIG. 3B is a diagram illustrating two pulse sequence series 301b, 302b each having two pulse sequence sets 310b, 320b that are each comprised of a plurality of pulse sequences with interlaced, biphasic DC pulses (e.g., 311b and 312b) to be delivered, respectively, to axially- and circumferentially-oriented electrode pairs in an electroporation electrode arrangement of the electroporation catheter. As shown, the pulse sequence sets 310b include axially-directed biphasic pulses 311b separated in time by an inter-pulse delay, and circumferentially-directed biphasic electrical pulses 312b temporarily interlaced with the axially-directed biphasic pulses. As further shown, in a given pulse sequence set 310b, the first circumferentially-directed electrical pulse 312b is generated during the inter-pulse delay between adjacent axially-directed electrical pulses 311b. It will be appreciated, however, that in other embodiments this order can be reversed. In the illustrated embodiment, the pulse sequence series 320b is substantially the same as the pulse sequence series 310b, except that in the pulse sequence series 320b the polarity of the circumferentially-directed electrical pulses 312b reverses from one pulse to the next.

With further reference to FIG. 3B, different sets of electrode pairs in the electroporation electrode arrangement may perform different pulse sequence series. A first set of electrode pairs may receive a first pulse sequence series 301b, and a second set of electrode pairs may receive a second pulse sequence series 302b. The first pulse sequence series 301b may be different from the second pulse sequence series 302b. In this way, for example, the electroporation electrode arrangement may have dedicated electrode pairs for generating electric fields in certain orientations. The first set of electrode pairs may generate one of an axially, transversely, or circumferentially orientated electric field, and the second set of electrode pairs may generate whichever of orientation the first set of electrodes did not. For example, as illustrated here, the first pulse sequence series 301b includes non-alternating pulses within pulse sequences (e.g., 312b within 301b) while the second pulse sequence series 302 includes alternating pulses within pulse sequences (e.g., 312b within 302b). The first and second pulse sequence series 301b, 302b may be synchronously or asynchronously generated and/or delivered to the electroporation electron arrangement. As described further hereinafter, if performed over time, these concepts may produce an electric field with dynamic gyration. Both the first and second set of electrode pairs may receive either the first or second pulse sequence series (e.g., 301b or 302b). In this way, the magnitude of the electric field in a given orientation may be increased over when only the first or second set of electrode pairs generates either the first or second pulse sequence series (e.g., 301b or 302b). Other pulse-manipulating techniques are helpful in increasing how effectively the electric field performs electroporation.

FIGS. 3C-3D are diagrams schematically illustrating alternative pulse sequence series 301c, 301d according to embodiments of the disclosure. As shown in FIG. 3C, the pulse sequence series 301c includes a plurality of alternating pulse sequences 305c, 306c separated in time by respective pauses. As shown, each pulse sequence 305c, 306c is made up of a series of biphasic DC electrical pulses 311c, 312c, respectively. In the illustrated embodiment, the pulse sequence 305c is delivered to axially-directed electrode pairs so as to generate a generally axially-oriented electric field, while the pulse sequence 306c is delivered to circumferentially-oriented electrode pairs so as to generate circumferentially-oriented electric fields. As discussed elsewhere herein, in embodiments, the aforementioned order can be reversed, and/or one of the pulse sequences 305c, 306c can be delivered to transversely-oriented electrode pairs.

In the embodiment of FIG. 3D, the pulse sequence series 301d comprises two electrical pulse sequences 305d separated by a predetermined pause, which are delivered to axially-oriented electrode pairs, followed by two electrical pulse sequences 306d separated by a predetermined pause and delivered to circumferentially-oriented electrode pairs. As with the embodiment of FIG. 3D, the aforementioned order can be reversed, and/or one of the pulse sequences 305d, 306d can be delivered to transversely-oriented electrode pairs.

It is emphasized that the disclosure should not be limited to the orientations shown in FIGS. 3A-3D. Although depicted in these figures as having axial and circumferential orientations, pulse sequences in this disclosure may include other combinations of orientations. For example, pulse sequences may include axial and transverse orientations, circumferential and transverse orientations, or each of axial, circumferential, and transverse orientations. Regardless of their form, pulse sequences may be arranged into pulse sequence sets and pulse sequence sets into pulse sequence series.

As discussed elsewhere herein, each of the generated pulse sequences delivered to the plurality of anode-cathode pairs may be charge-and-energy balanced, e.g., to prevent buildup of ionic byproducts and electrolysis and to help muscle stimulation. Although depicted and discussed with a certain number, orientation, or arrangement of pulse sequences, pulse sequence sets, or pulse sequence series, this disclosure should not be limited to such, as one skilled in the art would appreciate. As well, it is appreciated that pulse sequences may contain identical or different pulses and pulse sequence sets may contain identical or different pulse sequences.

Figure 3E:
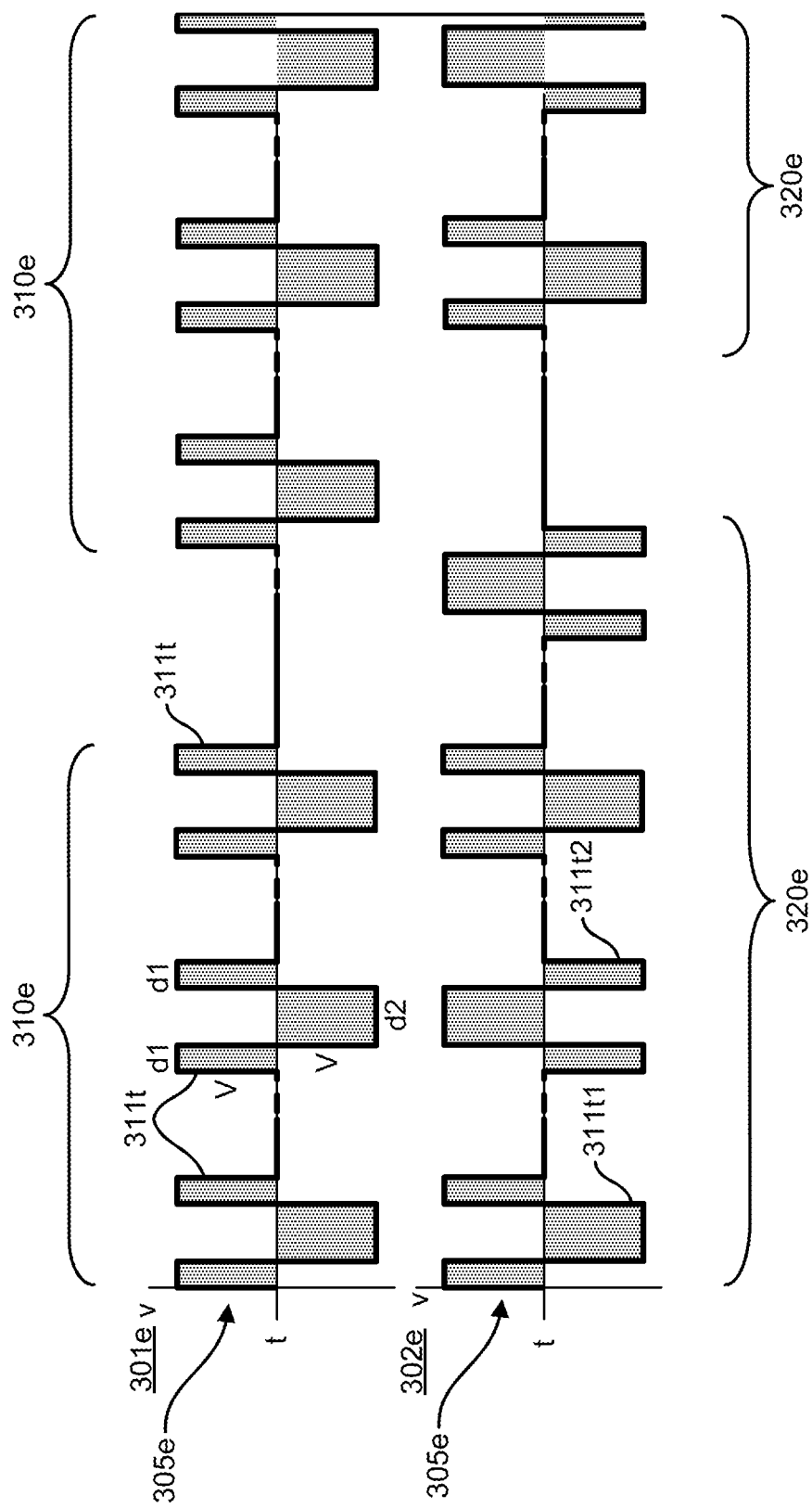
FIG. 3E is a diagram illustrating two pulse sequences, one non-alternating and the other alternating, of charge-and-energy balanced, symmetric triphasic pulses to be delivered to electrodes in an electroporation electrode arrangement of the catheter, in accordance with embodiments of the subject matter of the disclosure.
Figure 3F:
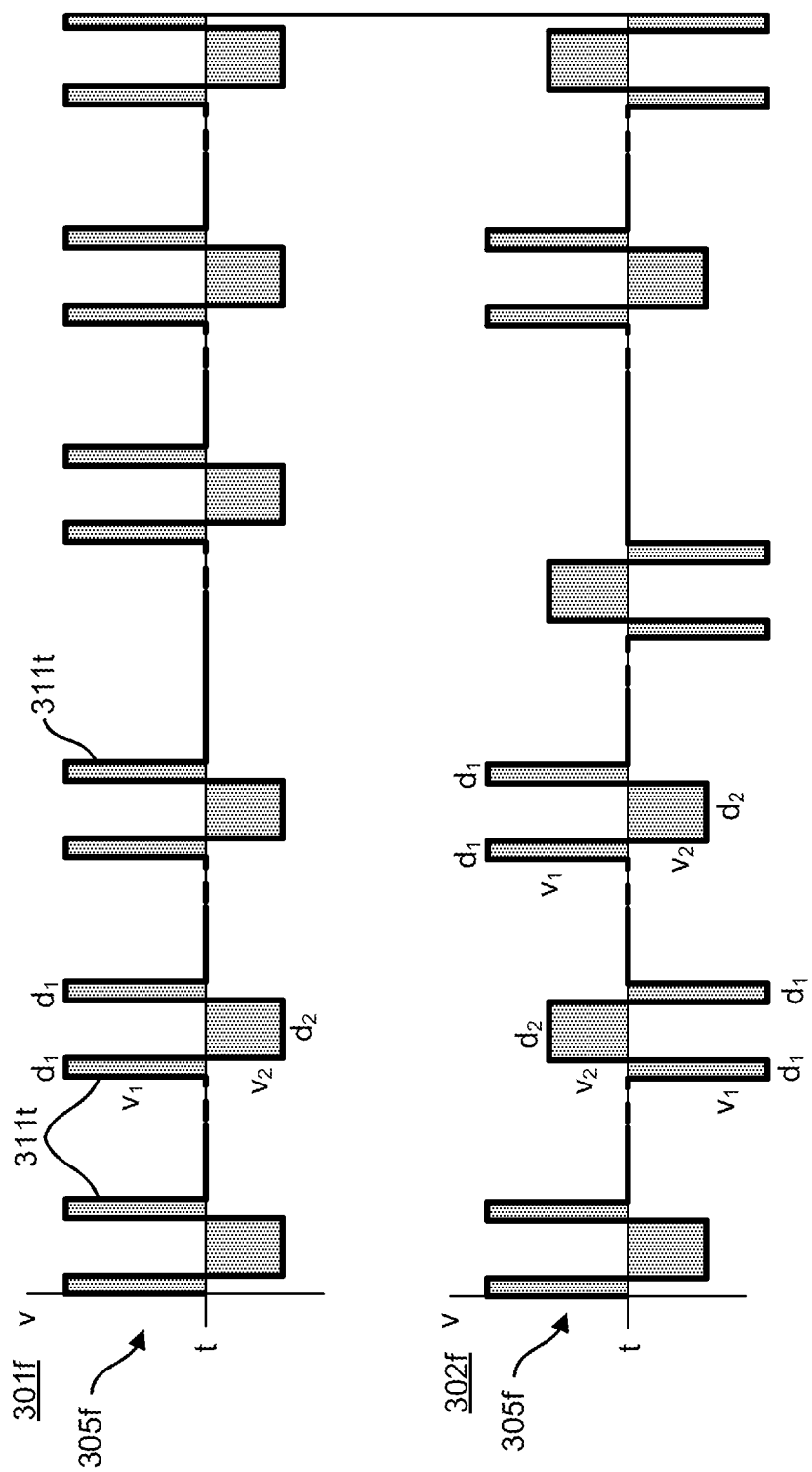
FIG. 3F is a diagram illustrating two pulse sequences, one non-alternating and the other alternating, of charge-and-energy balanced, asymmetric triphasic pulses to be delivered to electrodes in an electroporation electrode arrangement of the catheter, in accordance with embodiments of the subject matter of the disclosure.

FIG. 3E is a diagram illustrating two pulse sequences 305e, one non-alternating (301e) and the other alternating (302e), of charge-and-energy balanced, symmetric triphasic pulses (311t) to be delivered to electrodes in an electroporation electrode arrangement of the catheter. FIG. 3F. is a diagram illustrating two pulse sequences 305f, one non-alternating (301f) and the other alternating (302f), of charge-and-energy balanced, asymmetric triphasic pulses (311t) to be delivered to electrodes in an electroporation electrode arrangement of the catheter.

Referring to FIG. 3E, voltage shift and amplitudes may vary for a given pulse or between pulses according to embodiments of this disclosure. Rapid voltage shifts may open more pores in cell membranes. To produce this voltage shift, one or more pulses in a pulse sequence may have alternating polarity. For example, focusing on pulse sequence series 302e and pulse sequence set 310e therein, the one or more pulses may include a first pulse 311t1 and a second pulse 311t2. The second pulse 311t2 may be subsequent to the first pulse 311t1, and the first pulse 311t1 and the second pulse 311t2 may have alternating polarity. Triphasic pulses such as those shown in this figure create rapid voltage shifts within a pulse and may also do so between two pulses. For example, as shown, the first pulse 311t1 is a triphasic pulse that may alternate between positive, negative, and positive polarity, and the second pulse 311t2 is a triphasic pulse that alternates between negative, positive, and negative polarity. In embodiments, the first pulse 311t1 and second pulse 311t2 may be reversed without departing from the scope of this disclosure. As one skilled in the art would appreciate, these concepts may extend across any number of pulses. In addition, an increased number of open pores in cell membranes may be achieved in proportion to a high voltage amplitude, even for short pulse distances. Each of these concepts may be achieved while balancing charge and energy within the pulse sequence. The illustrated triphasic pulses have symmetric voltage amplitudes (v) and varied pulse lengths such that d1 is approximately equal to one half of d2 and are therefore charge-and-energy balanced. But depending on the desired application, these variables may proportionally vary to create higher voltage amplitudes with shorter pulse lengths and shorter voltage amplitudes with longer pulse lengths.

In embodiments, triphasic pulse sequences 305e, 305f may be delivered in a variety of forms while remaining charge-and-energy balanced. For example, boundary conditions may be established for each pulse and may include parameters for voltage amplitude and/or for pulse length. When the pulse sequences 305e, 305f delivered to the plurality of anode-cathode pairs comprise one or more triphasic pulses, each triphasic pulse may have a first voltage amplitude and a second voltage amplitude, the first voltage amplitude being greater than or equal to the second voltage amplitude. And each triphasic pulse may have a first voltage pulse length and a second voltage pulse length, the first voltage pulse length being less than or equal to the second voltage pulse length. The illustrated triphasic pulses have asymmetric voltage amplitudes (v) and varied pulse lengths such that d1 is less than d2 and are therefore charge-and-energy balanced while having a higher voltage amplitude than symmetric triphasic pulses (such as those shown in FIG. 3E). Regardless of form, pulse sequences such as those described above may be repeated during an electroporation operation to systematically open more pores in cell membranes.

In various embodiments, it may be advantageous to generate and selectively deliver to target tissue electrical pulse sequences that are not charge-balanced so as to promote electrolysis within the target tissue. Generally speaking, relatively short, high voltage electrical pulses are effective in causing reversible or irreversible electroporation in myocardial cells. In contrast, relatively long, low voltage electrical pulses can promote the formation of electrolytic byproducts in the myocardial tissue proximate the electrodes. These electrolytic byproducts can tend to diffuse outward along the electric field gradients and into the pores created in the cells via electroporation, thus causing, or at least encouraging, cell death due to an electrolytic imbalance within the cells. This technique can cause cell death in both irreversibly and reversibly electroporated cells. The present disclosure thus contemplates interlacing electrical pulses configured for causing irreversible electroporation with pulses configured for promoting the aforementioned electrolysis to enhance the likelihood of successfully ablating the target tissue.

Figure 3G:
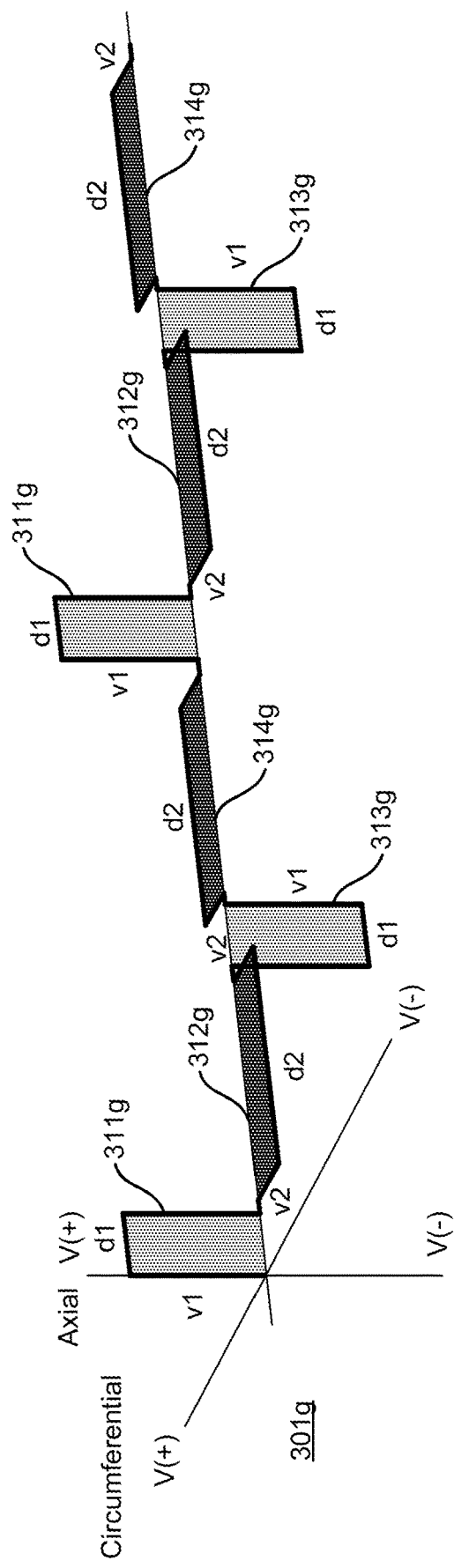
FIGS. 3G-3I are diagrams schematically illustrating exemplary charge-imbalanced pulse sequences to be delivered to delivered to electrodes in an electrode arrangement according to embodiments of subject matter of the disclosure.

FIG. 3G is a diagram schematically illustrating an exemplary pulse sequence series 301g comprised of interlaced axially-directed electrical pulses 311g, 313g, and circumferentially-directed electrical pulses 312g, 314g, with the electrical pulses 312g, 314g being interposed between adjacent electrical pulses 311g, 313g. As shown, the electrical pulses 311g, 313g are characterized by a pulse length d1 and a voltage V1, while the electrical pulses 312g, 314g are characterized by a pulse length d2 and a voltage V2. In embodiments, the pulse length d1 and the voltage V1 are relatively short and high, respectively, and are designed to ablate the target tissue by irreversible electroporation. Additionally, the pulse length d2 is substantially shorter than the pulse length d1, and the voltage V2 is substantially lower than the voltage V1. The resulting interlaced electric fields created at the respective electrode pairs to which the electrical pulses 311g, 312g, 313g and 314g are delivered can have the aforementioned dual effect of both ablating cells via irreversible electroporation and via cell death due to electrolytic imbalance.

Figure 3H:
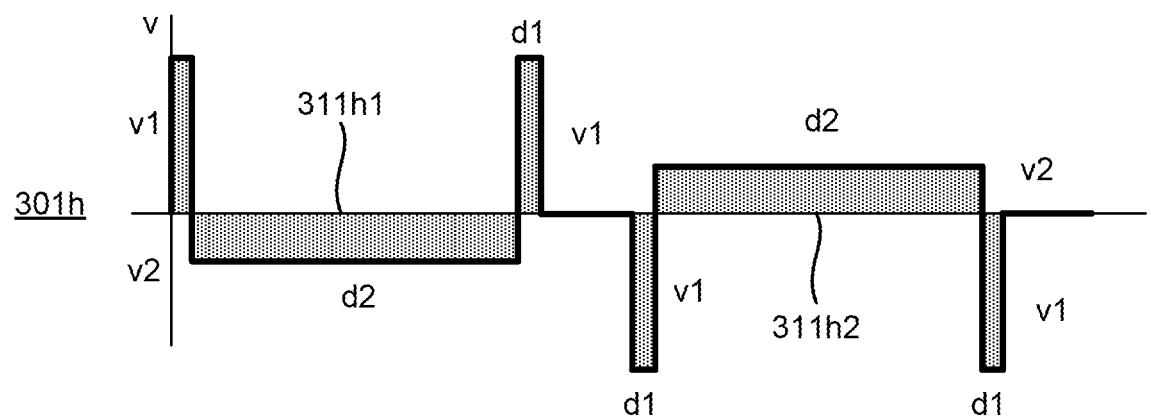
Figure 3I:
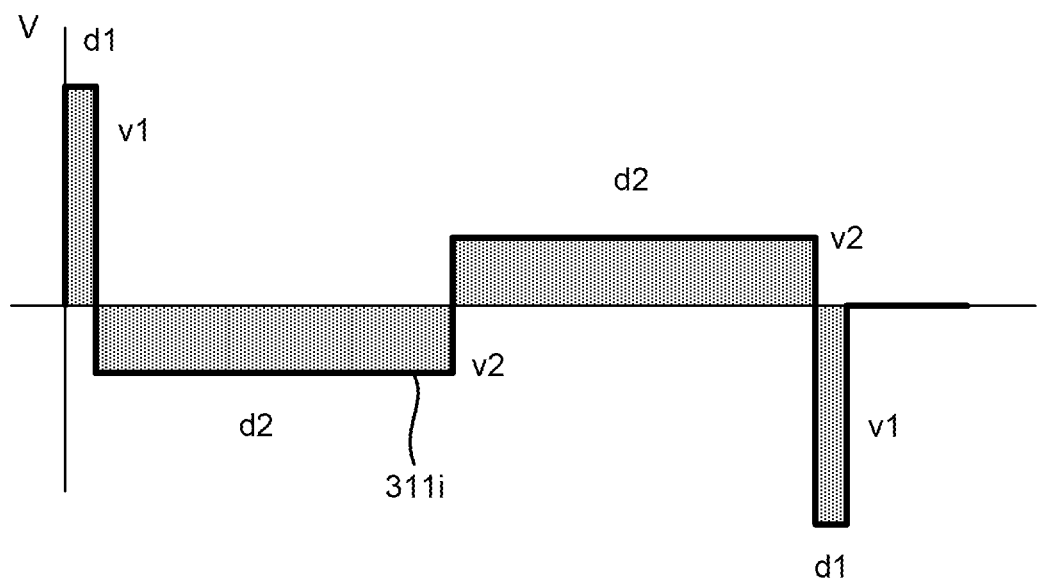

FIGS. 3H and 3I schematically illustrate additional exemplary electrical pulse forms that can be employed in the various embodiments to promote ablation via both irreversible electroporation and cell death by creating an electrolytic imbalance in the target cells. FIG. 3H illustrates a pulse sequence series 301h comprised of a plurality of triphasic, charge imbalanced electrical pulses 311h1, 311h2 each having first and third phases of the same polarity characterized by a phase length d1 and a voltage V1, and a second phase characterized by a phase length d2 and a voltage V2. The electrical pulse 311h2 differs from the electrical pulse 311h1 in that the polarity of each phase is opposite that of the corresponding phase in the electrical pulse 311h1, although in other embodiments each corresponding phase can have the same polarity. As shown, in embodiments, the phase lengths d1, d2 and the voltages V1, V2 can be selected to result in an overall charge imbalance of the electrical pulse 311h1 or 311h2, with the phase length d1 and voltage V1 selected to cause electroporation and the phase length d2 and the voltage V2 selected to promote electrolysis and the formation of an electrolytic imbalance leading to cell death.

A similar effect can be achieved by employing the quadphasic electrical pulse 311i illustrated schematically in FIG. 3I. As shown, the electrical pulse 311i is comprised of a first and fourth phase of opposite polarity and characterized by a phase length d1 and voltage V1, and second and third phases of opposite polarity each having the same phase length d2 and voltage V2. As shown, the phase length d1 is substantially shorter than the phase length d2, and the voltage V1 is substantially larger than the voltage V2, resulting in the aforementioned charge imbalance and corresponding dual-effect of causing cell death both by electroporation and electrolytic imbalance.

The electroporation generator may be configured to perform a feedback loop to loop the electroporation ablation system through a plurality of pulse sequences 305. In embodiments, the feedback loop may be automatic and/or may follow a programmed pattern. In either case, changes in orientation of the electric field may be continuous or intermittent. The feedback loop may be performed based on a target metric, such as electrogram amplitude reduction, impedance change, or another similar metric. When a target metric is achieved, for example, the electroporation generator may apply a generated pulse sequence across a different electrode pair than was previously used. As an example, the feedback loop may generate an axially oriented electric field followed by a transversely oriented electric field. It is appreciated that a feedback loop may also employ a mix of multidirectional and unidirectional electric fields in any order, and so this concept is not beyond the scope of this disclosure. Methods of this disclosure may make use of these concepts and of those described in relation to other embodiments disclosed herein.

Figure 4:
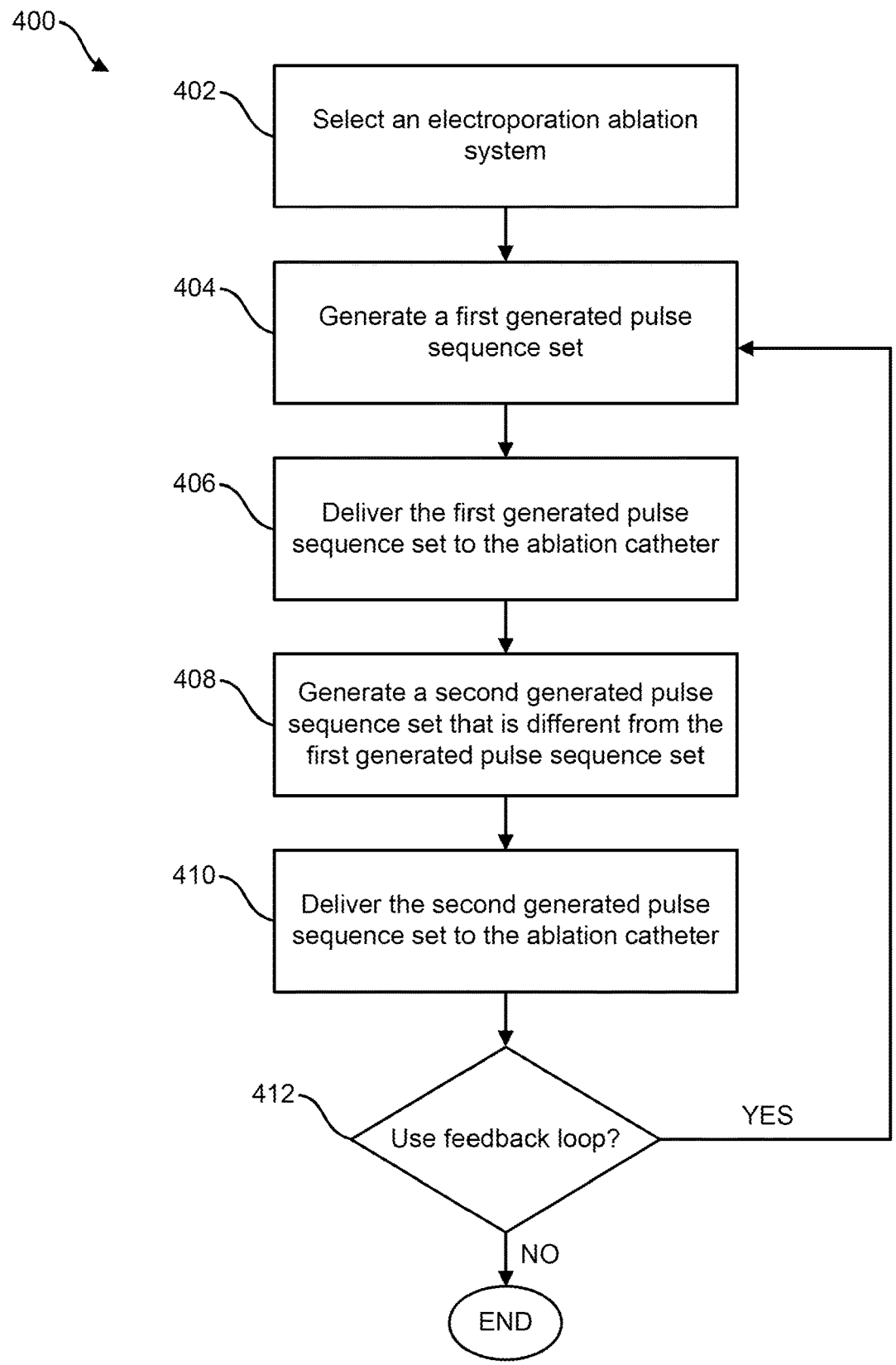
FIG. 4 is a diagram showing steps of a method of generating and delivering a signal to electrodes in an electroporation ablation system.

FIG. 4 is a diagram showing steps of a method 400 of generating and delivering a signal to electrodes in an electroporation ablation system. Such a method 400 and other related methods of generating and delivering a signal to electrodes in an electroporation ablation system are disclosed herein. Step 402 of the method 400 can include selecting an electroporation ablation system, which may be similar to those disclosed elsewhere herein. The method 400 may include generating, via the electroporation generator, a generated pulse sequence set including at least two of the first pulse sequence, the second pulse sequence, and the third pulse sequence. The method 400 may include delivering generated pulse sequence sets to the ablation catheter. Examples include generating a first generated pulse sequence set at step 404 and, at step 406, delivering the first generated pulse sequence set to the ablation catheter generating. At step 408, a second generated pulse sequence set may be generated and, at step 410, delivered to the ablation catheter. At step 412, the method 400 may include determining whether a feedback loop should be used as described hereinafter.

Generating a pulse sequence set can include generating a plurality of pulse sequence sets. At step 404, a first generated pulse sequence set may be generated, and at step 408, a second generated pulse sequence set that is different from the first generated pulse sequence set. For example, the first generated pulse set can be similar to those disclosed elsewhere herein, such as those with an axial orientation. And the second generated pulse set can be similar to those disclosed elsewhere herein, such as those with a circumferential orientation. In embodiments, generating the generated pulse sequence set may include alternatingly generating, over a time period, at least two of the first pulse sequence, the second pulse sequence, and the third pulse sequence to produce a dynamically gyrating electric field that comprises a changing pattern over the time period.

The gyrating electric field may be achieved via a feedback loop, such as those disclosed elsewhere herein. For example, at step 412, it may be determined whether to use a feedback loop. If so, the method 400 may loop back to a previous step such as step 404 to generate a first generated pulse sense set. And if no feedback loop is used at step 412, the method 400 may end.

In embodiments, delivering the generated pulse sequence set to the ablation catheter may employ sets of electrode pairs or depend on characteristic of the patient. For example, at step 408 a first generated pulse sequence may be applied across a first set of axially spaced electrodes, transversely spaced electrodes, or circumferentially spaced electrodes to produce a correspondingly oriented electric field. And at step 410 a second generated pulse sequence may be applied across whichever of the first set of axially spaced electrodes, transversely spaced electrodes, or circumferentially spaced electrodes that were not used in the first generated pulse sequence. In embodiments, the first and second generated pulse sequences may share at least one common electrode to which the first and second generated pulse sequences are applied. In embodiments, alternating waveforms may be delivered at different stages of the cardiac cycle (e.g., using local EGM sensing).

Various modifications and additions may be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. An electroporation ablation system for treating target tissue, the electroporation ablation system comprising:
  an ablation catheter including:
    a handle;
    a shaft having a distal end and defining a longitudinal axis of the ablation catheter; and
    an electroporation electrode arrangement at the distal end of the shaft and including a plurality of electrodes spatially arranged in a three-dimensional electrode structure about the longitudinal axis so as to generate a plurality of electric fields when a plurality of electrical pulse sequences are delivered to selected pairs of the plurality of electrodes, the plurality of electric fields including a first electric field having a first orientation relative to the longitudinal axis, and second electric field having a second orientation relative to the longitudinal axis, wherein at least one of the first orientation and second orientation is generally aligned with the longitudinal axis; and
  an electroporation generator operatively coupled to the electroporation electrode arrangement and configured to selectively generate and deliver:
    a first electrical pulse sequence to a first selected pair of electrodes to generate the first electric field, the first electrical pulse sequence comprising a plurality of first monophasic direct current (DC) pulses each having a first voltage and a first pulse length, wherein sequential first monophasic pulses have opposite polarities and are separated by a first predetermined inter-pulse delay; and
    a second electrical pulse sequence to a second selected pair of electrodes to generate the second electric field, the second electrical pulse sequence comprising a plurality of second monophasic DC pulses each having a second voltage and a second pulse length, wherein the second voltage is lower than the first voltage, and wherein the second pulse length is greater than the first pulse length, and wherein sequential second monophasic DC pulses have opposite polarities and are separated by a second predetermined inter-pulse delay, and
    wherein the electroporation generator is further configured to deliver each second monophasic DC pulse during one of the first inter-pulse delays.

2. The electroporation ablation system of claim 1, wherein the first orientation is generally aligned with the longitudinal axis, and wherein the second orientation is circumferential about the longitudinal axis.

3. The electroporation ablation system of claim 1, wherein the first orientation is generally aligned with the longitudinal axis, and wherein the second orientation is transverse to the longitudinal axis.

4. An electroporation ablation system for treating target tissue, the electroporation ablation system comprising:
  an ablation catheter including:
    a handle;
    a shaft having a distal end and defining a longitudinal axis of the ablation catheter; and
    an electroporation electrode arrangement at the distal end of the shaft and including a plurality of electrodes arranged in a three-dimensional electrode structure about the longitudinal axis so as to define a plurality of electrode pairs each configured to generate an electric field when an electrical pulse sequence is delivered thereto, the plurality of electrode pairs including:
      a first electrode pair arranged so as to generate a first electric field having a first orientation relative to the longitudinal axis when a first electrical pulse sequence is delivered thereto; and
      a second electrode pair arranged so as to generate a second electric field having a second orientation relative to the longitudinal axis when a second electrical pulse sequence is delivered thereto;
    wherein at least one of the first orientation and second orientation is generally aligned with the longitudinal axis; and
  an electroporation generator operatively coupled to the electroporation electrode arrangement and configured to selectively generate and deliver the first electrical pulse sequence to the first electrode pair, and the second electrical pulse sequence to the second electrode pair, wherein the first electrical pulse sequence comprises a plurality of first monophasic direct current (DC) pulses each having a first voltage and a first pulse length, wherein sequential first monophasic DC pulses have opposite polarities and are separated by a first predetermined inter-pulse delay, and wherein the second electrical pulse sequence comprises a plurality of second monophasic DC pulses each having a second voltage and a second pulse length, wherein the second voltage is lower than the first voltage, and wherein the second pulse length is greater than the first pulse length, and wherein sequential second monophasic DC pulses have opposite polarities and are separated by a second predetermined inter-pulse delay, and wherein the electroporation generator is further configured to deliver each second monophasic DC pulse during one of the first inter-pulse delays.

5. The electroporation ablation system of claim 4, wherein the first orientation is generally aligned with the longitudinal axis, and wherein the second orientation is circumferential about the longitudinal axis.

6. The electroporation ablation system of claim 4, wherein the first orientation is generally aligned with the longitudinal axis, and wherein the second orientation is transverse to the longitudinal axis.

7. A method of generating and delivering a signal to electrodes in an electroporation ablation system, the method comprising:

delivering a first electrical pulse sequence to a first electrode pair of an electroporation catheter having a longitudinal axis in a three-dimensional electrode structure about the longitudinal axis so as to generate a first electric field having a first orientation relative to the longitudinal axis, wherein the first electrical pulse sequence comprises a plurality of first monophasic direct current (DC) pulses each having a first voltage and a first pulse length, wherein sequential first monophasic DC pulses have opposite polarities and are separated by a first predetermined inter-pulse delay; and delivering a second electrical pulse sequence to a second electrode pair of the electroporation catheter so as to generate a second electric field having a second orientation relative to the longitudinal axis, wherein the second electrical pulse sequence comprises a plurality of second monophasic DC pulses each having a second voltage and a second pulse length, wherein the second voltage is lower than the first voltage, and wherein the second pulse length is greater than the first pulse length, and wherein sequential second monophasic DC pulses have opposite polarities and are separated by a second predetermined inter-pulse delay, and each second monophasic DC pulse is delivered during one of the first inter-pulse delays, and wherein at least one of the first orientation and second orientation is generally aligned with the longitudinal axis.

8. The method of claim 7, wherein delivering the first electrical pulse sequence to the first electrode pair and delivering the second electrical pulse sequence to the second electrode pair includes alternatingly delivering, over a time period, the first electrical pulse sequence to the first electrode pair and delivering the second electrical pulse sequence to the second electrode pair to produce a dynamically gyrating electric field that comprises a changing pattern over the time period.

9. The method of claim 8, wherein the first orientation is generally aligned with the longitudinal axis, and wherein the second orientation is circumferential about the longitudinal axis.

10. The method of claim 8, wherein the first orientation is generally aligned with the longitudinal axis, and wherein the second orientation is transverse to the longitudinal axis.

* * * * *